United States Patent
Hanson et al.

(10) Patent No.: US 9,504,526 B2
(45) Date of Patent: Nov. 29, 2016

(54) NAVIGATION INSTRUMENTS FOR SUBCHONDRAL BONE TREATMENT

(71) Applicant: ZIMMER KNEE CREATIONS, INC., Exton, PA (US)

(72) Inventors: Shaun B. Hanson, West Chester, PA (US); Christopher D. Mandeen, West Chester, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 336 days.

(21) Appl. No.: 14/022,001

(22) Filed: Sep. 9, 2013

(65) Prior Publication Data

US 2014/0074117 A1    Mar. 13, 2014

Related U.S. Application Data

(60) Provisional application No. 61/698,240, filed on Sep. 7, 2012.

(51) Int. Cl.

| | |
|---|---|
| *A61B 19/00* | (2006.01) |
| *A61M 5/32* | (2006.01) |
| *A61B 17/3211* | (2006.01) |
| *A61B 17/32* | (2006.01) |
| *A61M 5/46* | (2006.01) |
| *A61B 17/17* | (2006.01) |
| *A61B 17/34* | (2006.01) |
| *A61B 17/88* | (2006.01) |
| *A61B 17/00* | (2006.01) |

(52) U.S. Cl.
CPC ......... *A61B 19/201* (2013.01); *A61B 17/1764* (2013.01); *A61B 17/3211* (2013.01); *A61B 17/320016* (2013.01); *A61B 17/3403* (2013.01); *A61B 90/11* (2016.02); *A61M 5/3287* (2013.01); *A61M 5/46* (2013.01); *A61B 17/8805* (2013.01); *A61B 2017/0046* (2013.01); *A61B 2017/3411* (2013.01); *A61B 2090/3966* (2016.02)

(58) Field of Classification Search
CPC combination set(s) only.
See application file for complete search history.

(56) References Cited

U.S. PATENT DOCUMENTS

| | | |
|---|---|---|
| 5,514,137 A | 5/1996 | Coutts |
| 5,556,429 A | 9/1996 | Felt |
| 5,755,809 A | 5/1998 | Cohen |
| 6,140,452 A | 10/2000 | Felt |
| 6,235,043 B1 | 5/2001 | Reiley |
| 6,241,734 B1 | 6/2001 | Scribner |
| 6,248,110 B1 | 6/2001 | Reiley |
| 6,306,177 B1 | 10/2001 | Felt |
| 6,395,007 B1 | 5/2002 | Bhatnagar |

(Continued)

FOREIGN PATENT DOCUMENTS

| | | |
|---|---|---|
| WO | WO-2012116089 A1 | 8/2012 |
| WO | WO-2014053913 A2 | 4/2014 |
| WO | WO-2014053913 A3 | 4/2014 |

OTHER PUBLICATIONS

Specification for U.S. Appl. No. 14/021,785, filed Sep. 9, 2013.

(Continued)

*Primary Examiner* — Sameh Boles
(74) *Attorney, Agent, or Firm* — Schwegman Lundberg & Woessner, P.A.

(57) ABSTRACT

Navigation instruments and guides for targeting a subchondral region of bone and subchondral bone defects are provided. The instruments and guides may be used in reference to an anatomical landmark of a joint.

15 Claims, 26 Drawing Sheets

(56) References Cited

U.S. PATENT DOCUMENTS

| | | |
|---|---|---|
| 6,564,083 B2 | 5/2003 | Stevens |
| 6,607,561 B2 | 8/2003 | Brannon |
| 6,613,054 B2 | 9/2003 | Scribner |
| 6,719,761 B1 | 4/2004 | Reiley |
| 6,746,451 B2 | 6/2004 | Middleton |
| 6,827,720 B2 | 12/2004 | Leali |
| 6,863,899 B2 | 3/2005 | Koblish |
| 6,887,246 B2 | 5/2005 | Bhatnagar |
| 7,153,307 B2 | 12/2006 | Scribner |
| 7,261,720 B2 | 8/2007 | Stevens |
| 7,708,742 B2 | 5/2010 | Scribner |
| 7,771,431 B2 | 8/2010 | Scribner |
| 7,811,290 B2 | 10/2010 | Rabiner |
| 8,062,364 B1 | 11/2011 | Sharkey et al. |
| 8,152,813 B2 | 4/2012 | Osorio |
| 8,168,692 B2 | 5/2012 | Wenz |
| 2003/0138473 A1 | 7/2003 | Koblish |
| 2005/0119219 A1 | 6/2005 | Bellini |
| 2006/0064164 A1 | 3/2006 | Thelen |
| 2010/0076503 A1 | 3/2010 | Beyar |
| 2010/0179549 A1 | 7/2010 | Keller |
| 2011/0125156 A1 | 5/2011 | Sharkey et al. |
| 2011/0125157 A1 | 5/2011 | Sharkey et al. |
| 2011/0125159 A1 | 5/2011 | Hanson et al. |
| 2011/0125200 A1* | 5/2011 | Hanson ............... A61B 17/1764 606/86 R |
| 2011/0125201 A1 | 5/2011 | Hanson et al. |
| 2011/0125264 A1 | 5/2011 | Bagga et al. |
| 2011/0125265 A1 | 5/2011 | Bagga et al. |
| 2011/0125272 A1 | 5/2011 | Bagga et al. |
| 2012/0245645 A1* | 9/2012 | Hanson ............... A61B 17/1764 606/86 R |
| 2012/0316513 A1 | 12/2012 | Sharkey et al. |

OTHER PUBLICATIONS

"International Application Serial No. PCT/IB2013/002672, International Preliminary Report on Patentability mailed Mar. 19, 2015", 12 pgs.

"International Application Serial No. PCT/IB2013/002672, International Search Report mailed May 28, 2014", 7 pgs.

"International Application Serial No. PCT/IB2013/002672, Invitation to Pay Additional Fees and Partial Search Report mailed Mar. 18, 2014", 6 pgs.

"International Application Serial No. PCT/IB2013/002672, Written Opinion mailed May 28, 2014", 10 pgs.

* cited by examiner

NAVIGATION INSTRUMENTS FOR SUBCHONDRAL BONE TREATMENT

CROSS-REFERENCE TO RELATED APPLICATIONS

This application claims priority to U.S. Provisional No. 61/698,240 filed Sep. 7, 2012 and entitled "NAVIGATION INSTRUMENTS FOR SUBCHONDRAL BONE TREATMENT," the contents of which are incorporated by reference in their entirety.

FIELD

The present invention relates to tools for the surgical treatment of joints, and more particularly to instruments and associated methods for the surgical repair and treatment of bone tissue at these joints. Even more particularly, the present invention relates to navigation instruments for targeting an area near a subchondral bone defect using anatomical landmarks.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in joints such as the knee and ankle, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, microfracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

In current practice, surgeons typically "eyeball" (i.e., visually estimate) the target site on a bone to be repaired. Most conventional targeting and location methods are relatively crude and provide little guidance to a surgeon during the actual surgical procedure. Accordingly, it would be desirable to provide methods and instruments in which the area near a bone defect can be easily located and provide a reference framework that can be used in a surgical procedure irrespective of the approach. Furthermore, in some situations where pinpoint accuracy is not critical or necessary, a navigation system that can indicate an area sufficiently near the bone defect in a quick and reliable manner would be highly beneficial to the clinician.

Accordingly, it is desirable to provide instruments that allow fast, easy, and repeatable navigation to an area sufficiently near a bone defect to be treated. It is further desirable to provide instruments that do not obstruct access to the working area around the target site, and allow as clear a view as possible for the clinician.

SUMMARY

The present disclosure provides navigation instruments for targeting an area sufficiently near a subchondral bone defect using anatomical landmarks. The instruments allow the surgeon to navigate to the area around the bone defect quickly and easily, while also facilitating proper insertion of a tool or other device into an appropriate area near the defect.

In one embodiment, an instrument for navigating to a target area near a subchondral defect of a bone is provided. The instrument may comprise a guide having a plurality of device portals, each portal defining a trajectory and configured to provide accurate and controlled delivery of a tool to the target area. Also provided is a handle extending from the guide. The handle may be detachable. The instrument may be configured to align with an anatomical landmark of the bone, and include visual markers to assist in positioning the instrument. In one embodiment, the guide is configured to target a subchondral area of the tibia. In another embodiment, the guide is configured to target a subchondral area of the femur, and may comprise a hinged pair of arms.

In some embodiments, the instrument may further include visual markers for vertical alignment of the instrument. In addition, the detachable handle may include a guide attachment end having a plurality of keyed slots. The guide component may comprise a shaped stem that is configured to engage one or more of the keyed slots of the handle, thus allowing the guide to be angularly adjustable relative to the detachable handle. The instrument may receive a tool such as an injection needle that may include a depth gauge.

In another exemplary embodiment, an instrument for navigating to a target area near a subchondral defect of a bone is provided. The instrument may comprise a guide having a horizontal approach device portal and a distal approach device portal, each portal defining a trajectory and configured to provide accurate and controlled delivery of a tool to the target area. The instrument may also comprise a handle extending from the guide. The guide and handle may comprise a uniform body. In addition, the instrument may be configured to align with an anatomical landmark of the bone, and include visual markers to assist in positioning the instrument.

In some embodiments, the handle may be configured to secure to a patient's leg. The instrument may also include a slot for insertion of a scalpel. The instrument may be configured to align with an anatomical landmark of the bone, and include visual markers to assist in positioning the instrument. In one embodiment, the guide is configured to target a subchondral area of the tibia. The instrument may receive a tool such as an injection needle that may include a depth gauge.

In still another exemplary embodiment, a system for navigating to a target area near a subchondral defect of a bone is provided. The system may comprise a handle component comprising a slot for receiving a guide component, a femoral guide component comprising a hinged pair of arms, and a tibial guide component. Each of the guide components may comprise a plurality of device portals, each portal defining a trajectory and configured to provide accurate and controlled delivery of a tool to the target area. Furthermore, each of the guide components may be slidingly received in the slot of the handle component. The slot of the handle component may comprise a plurality of keyed sections or notches. Each of the guide components may comprise a shaped stem configured to engage one or more of the keyed sections or notches of the slot of the handle. The guide components may be angularly adjustable relative to the handle.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1:
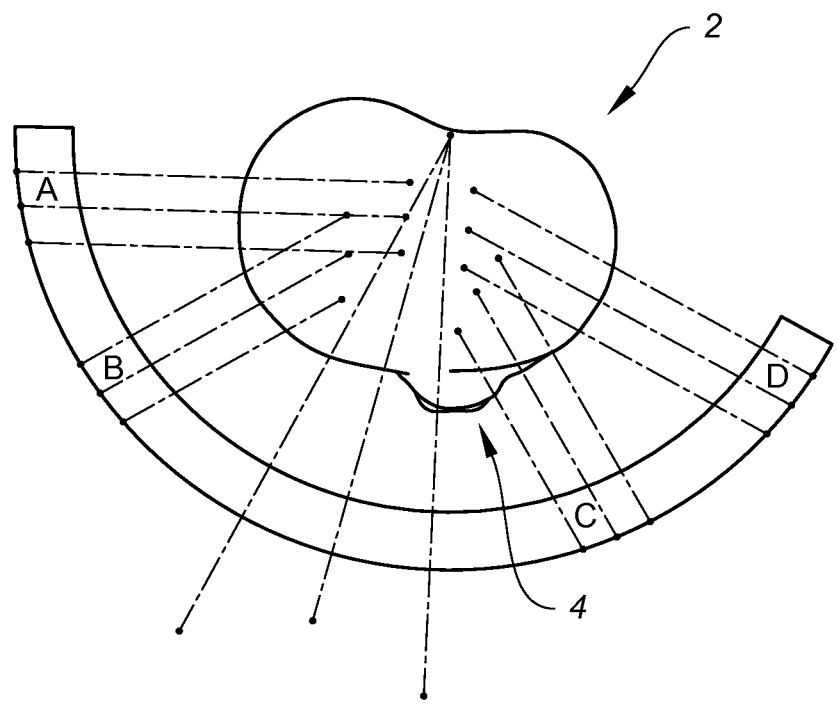
FIG. 1 is top-down perspective view of an exemplary embodiment of a navigation instrument of the present disclosure relative to a tibia.

Methods, devices and instruments for treating joint pain to restore natural joint function and preserving, as much as possible, the joint's articular and cartilage surface are known. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,364 entitled "OSTEOARTHRITIS TREATMENT AND DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In an SCP™ procedure, bone fractures or non-unions are stabilized, integrated or healed, which results in reduction of a bone defect, such as a bone marrow lesion or edema. In addition, the SCP™ procedure restores or alters the distribution of forces in a joint to thereby relieve pain. The SCP™ procedure can be performed arthroscopically or percutaneously to treat pain by stabilizing chronic stress fracture, resolving any chronic bone marrow lesion or edema, and preserving, as much as possible, the articular surfaces of the joint. The SUBCHONDROPLASTY™ procedure generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for the SCP™ procedure for the different extents of treatment needed can be employed. Accordingly, a medical practitioner may elect to use the techniques and devices described herein to subchondrally treat any number of bone defects, as he deems appropriate.

Detection and identification of the relevant bone marrow lesion or bone marrow edema (BML or BME) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

The SCP™ treatment may continue after surgery. In particular, the patient may be monitored for a change in pain scores, or positive change in function. For example, patients are also checked to see when they are able to perform full weight-bearing activity and when they can return to normal activity. Of note, the SCP™ procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP™ treated area may remain undisturbed while the additional treatment is performed, such as where cartilage resurfacing is desired. Alternatively, the SCP™ treated area can be removed, and not create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement.

Various surgical treatments to address subchondral defects known as bone marrow lesions have previously been attempted. Between May and November 2008, three (3) surgeries were performed at Riddle Hospital in Media, Pa. in the United States. On May 12, 2008, Dr. Peter F. Sharkey performed a right knee arthroscopy with arthroscopically assisted stabilization of a patient's right knee with a medial tibial plateau fracture. During the procedure, a cannulated bone biopsy needle was placed into the bone under fluoroscopic guidance, and augmentation material was injected. The injected augmentation material was Stryker Orthopedics Hydroset (Bone Substitute Material). The surgeon expressed difficulty in injecting the bone substitute material.

On Oct. 27, 2008, Dr. Steven B. Cohen performed a left knee arthroscopy, partial medial meniscectomy, drilling of osteochondral lesion using retrograde technique, and debridement chondroplasty of patellofemoral chondrosis on a patient's left knee with medial meniscus tear and left knee osteochondral defect with bone marrow lesion of the medial femoral condyle. During the procedure, an Anterior Cruciate Ligament (ACL) portal-creation device was repurposed for this surgery. The tibial probe was placed on the medial femoral condyle, with the tunnel guide secured proximally on the thigh. The surgeon expressed difficulty in positioning and stabilizing the guide. A cannulated pin was placed through the tunnel guide and placed distally into the medial femoral condyle. No implantable material was injected into the bone in this case.

On Nov. 10, 2008, Dr. Steven B. Cohen performed a right knee arthroscopic-assisted repair of a tibial plateau fracture bone marrow lesion with subchondral fracture using bone cement, partial medial and partial lateral meniscectomy to treat medial meniscus tear, and arthroscopic debridement and chondroplasty of medial, lateral, and patellofemoral compartments to treat compartment chondrosis. During the procedure, a guide pin was inserted into the medial tibial plateau, and an endo button drill bit was used to expand the drill hole. One (1) cubic centimeter (cc) of cement was inserted into the bone. A second drill hole was made from below, and a second cubic centimeter (cc) of cement was inserted into the bone.

The experiences gained from these previous surgeries helped to develop the fundamental theories underlying the SUBCHONDROPLASTY™ procedure and the number of treatment modalities, associated devices, instruments and related methods of use for performing the SUBCHONDROPLASTY™ procedure, which are disclosed in the aforementioned publications. These treatment modalities may be used alone or in combination, as will be described in detail below.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In an SCP™ procedure, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in an SCP™ procedure. For instance, stimulation of bone tissue in an SCP™ procedure may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect (s). Suitable implantable fixation devices for the surgical treatment of these altered bone regions or bone defects, especially at the subchondral level, are disclosed in co-pending and co-owned U.S. Patent Application Publication No. 2011/0125265 entitled "IMPLANTABLE DEVICES FOR SUBCHONDRAL TREATMENT OF JOINT PAIN," U.S. Patent Application Publication No. 2011/0125264 entitled "IMPLANTABLE DEVICES FOR SUBCHONDRAL TREATMENT OF JOINT PAIN," and U.S. Patent Application Publication No. 2011/0125272 entitled "BONE-DERIVED IMPLANTABLE DEVICES FOR SUBCHONDRAL TREATMENT OF JOINT PAIN," all of which were filed on Nov. 19, 2010, the contents of which are herein incorporated in their entirety by reference. These devices and instruments can be use in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out or degenerate locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, restoration of normal physiologic stress distribution can be achieved in load bearing joints such as the hip and knee, and mechanical congruity restored, thereby resulting in healing of the inflammation and reduction or elimination of pain.

In general, the present disclosure provides embodiments related to instruments and associated methods for the surgical treatment of a joint, and particularly a bone defect at that joint region. More specifically, the embodiments relate to instruments for treating a bone defect of a joint at the subchondral level and associated methods. These instruments and devices may be used in a manner consistent with the subchondral procedures previously described.

As previously mentioned, instruments and tools to carry out the SCP™ techniques mentioned above, such as navigation instruments and guides for targeting a subchondral region of bone and subchondral bone defects, have been disclosed by applicants. Such navigation or imaging tools or guides may be used to ascertain a desired access path for targeting the location of the subchondral region near the subchondral defect to be treated. In one example, this access path may be determined using a mapping system that provides a set of coordinates for targeting the location of the subchondral region. Such a mapping system may be similar to the one disclosed in co-pending and co-owned U.S. Patent Application Publication No. 2011/0125201, filed Nov. 19, 2010 and entitled "COORDINATE MAPPING SYSTEM FOR JOINT TREATMENT," the contents of which are herein incorporated in their entirety by reference.

In addition to the mapping system described above, other navigation or imaging tools suitable for use with the systems and methods of the present disclosure may include those disclosed in co-pending and co-owned U.S. Patent Application Publication No. 2011/0125159, filed Nov. 19, 2010 and entitled "INSTRUMENTS FOR A VARIABLE ANGLE APPROACH TO A JOINT," U.S. Patent Application Publication No. 2011/0125200, filed Nov. 19, 2010 and entitled "NAVIGATION AND POSITIONING INSTRUMENTS FOR JOINT REPAIR AND METHODS OF USE," and U.S. Patent Application Publication No. 2012/0245645, filed Feb. 22, 2012 and entitled "NAVIGATION AND POSITIONING SYSTEMS AND GUIDE INSTRUMENTS FOR JOINT REPAIR," the contents of which are herein incorporated in their entirety by reference.

The present disclosure provides alternative embodiments of these types of navigation instruments that are simpler and require fewer steps to implement. These navigation instruments eliminate the need to pin the instrument to the bone, are compatible with more injection systems, and may also provide depth control. In addition, the navigation instruments of the present disclosure eliminate the need for posterior edge alignment, thus enabling a faster procedure by reducing the time of surgery and time and amount of C-arm fluoroscopic or x-ray exposure to the patient. Additional, the navigation instruments of the present disclosure may be disposable. If desired, these navigation instruments may also be tied into a template system, similar to those previously described by applicants.

The present disclosure provides at least two varieties of navigation instruments: one for frame navigation that may require MRI/template assisted targeting, another for free hand navigation that does not require MRI/template assisted targeting. Both versions still employ basic principles outlined in applicants' previous disclosures relating to template and targeting instruments. For instance, a template map is still used to target the SCP target location in the bone, and anatomy, fluoroscopic, x-ray, or guide fixtures to align 3-dimensionally and target the injection system to the lesion are still applicable.

Figure 2:
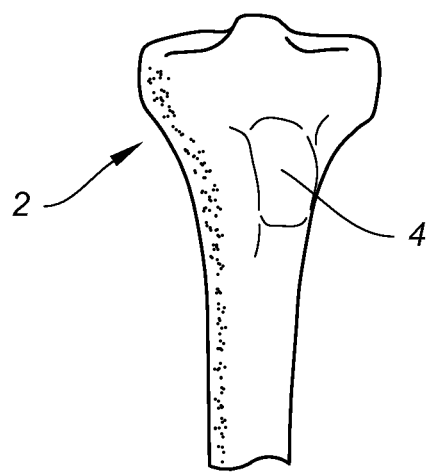
FIG. 2 is a perspective view of a tibial bone and anatomical landmark used with navigation instruments of the present disclosure.
Figure 3:
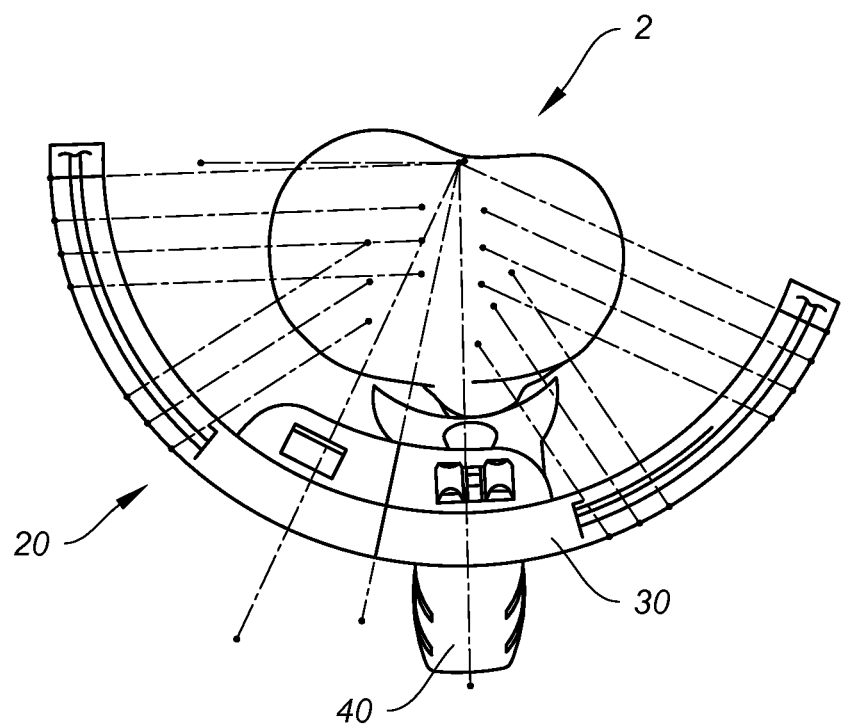
FIG. 3 is another top-down perspective view of the navigation instrument of FIG. 1 relative to a tibia.

Turning now to the drawings, FIG. 1 shows a guide 30 of a navigation instrument 20 relative to a tibia 2. Principles of targeting with a template as previously disclosed by applicants may still apply here. Similar to those previous techniques, the tibia 2 is mapped out into separate targeting zones correlating to the instrument 20. The anatomical reference is the tibial tuberosity, as shown here in FIG. 2. The tibial tuberosity 4 is usually visible and can be palpated below the skin. It is also visible on X-ray and on MRI. The location is fairly consistent and can be used as an anatomical landmark by the navigation instruments of the present disclosure. The template and guide are provided in both a Left Knee and Right Knee version so as to be specific to match the anatomical geometry of the tibia 2 and tuberosity 4. FIG. 3 shows the top part of the guide 30 corresponding to the template zones and tibia plateau.

Figure 4:
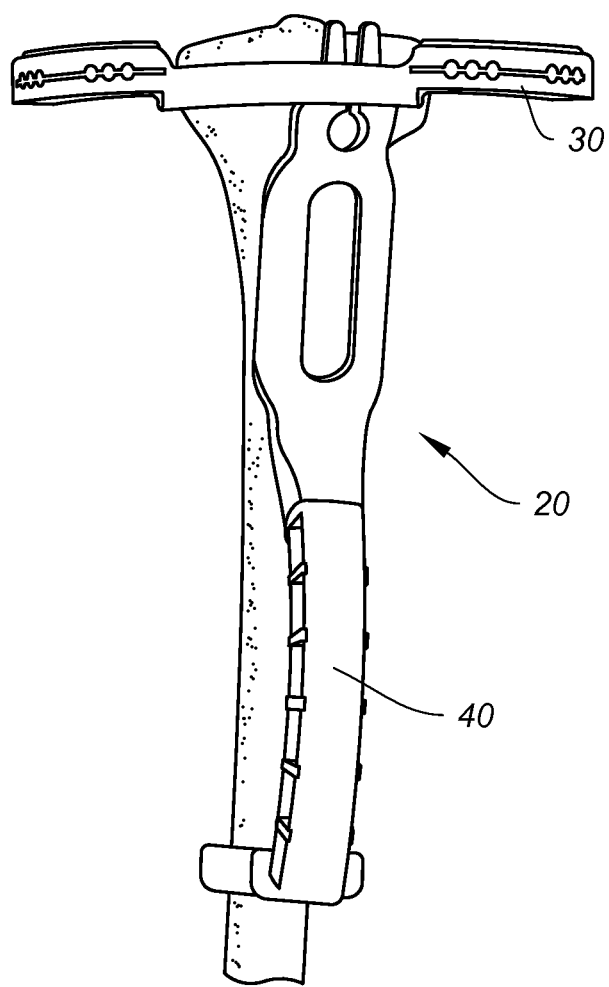
FIG. 4 shows a front view of the navigation instrument of FIG. 1 relative to a tibia.

FIG. 4 shows that the handle 40 of the instrument 20 has a geometry that fits securely over the tibial tuberosity 4, allowing the instrument 20 to use the tibial tuberosity 4 as an anatomical reference point. The handle 40 aligns to the tibial axis and to the tuberosity 4 creating a stable frame on the leg. The axis angle of tibial axis to the plateau is built into the handle 40, as further shown in FIG. 10.

Figure 5B:
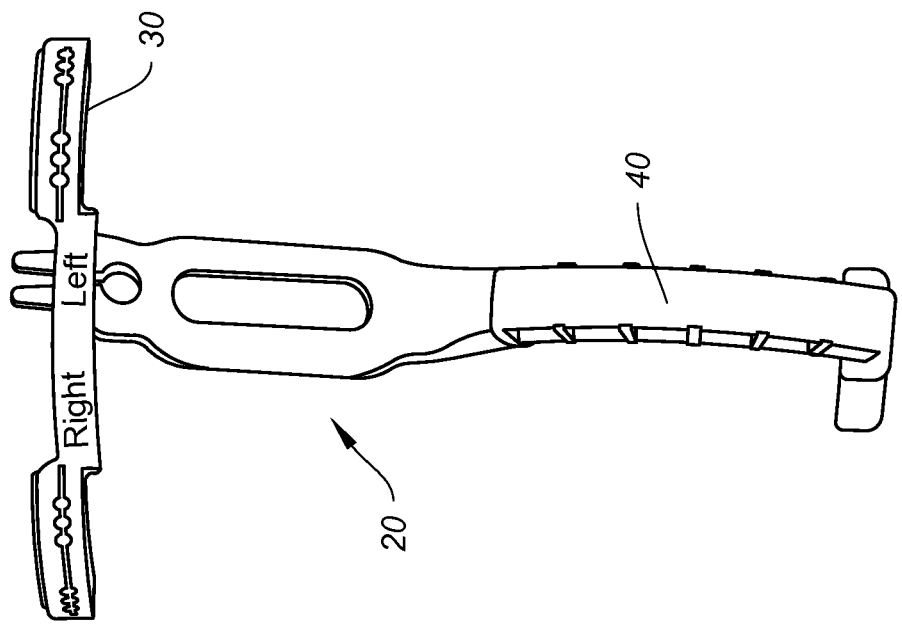
FIGS. 5A and 5B show a right and left version of the navigation instrument of FIG. 4, respectively.
Figure 5A:
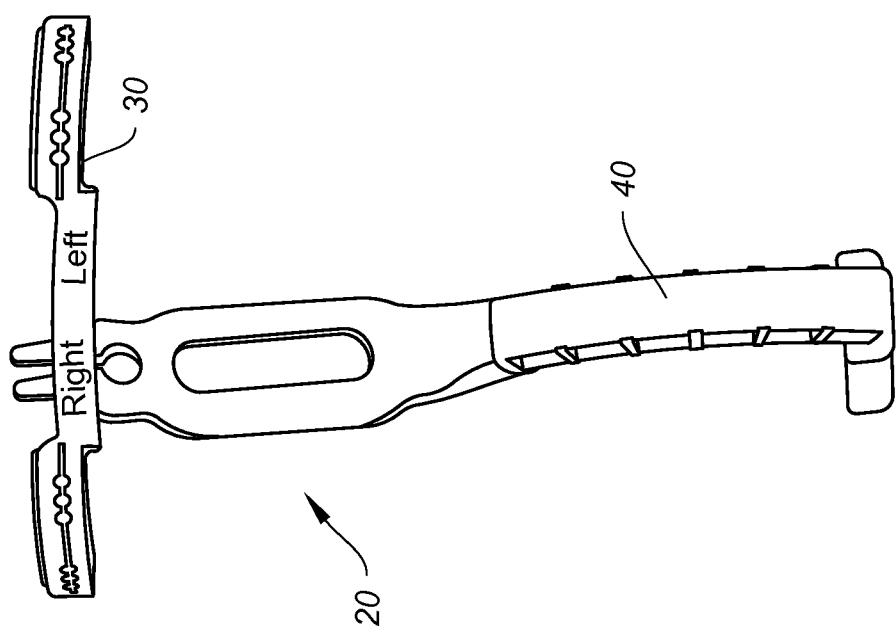

As mentioned, the handle 40 and guide 30 are separable components and are attachable in two different positions for the Left or Right knee. This allows for specific anatomical alignment and secure fit to either Left or Right side being treated. A Right Knee and Left Knee version of the navigation instrument 20 are shown in FIGS. 5A and 5B, respectively.

Figure 6:
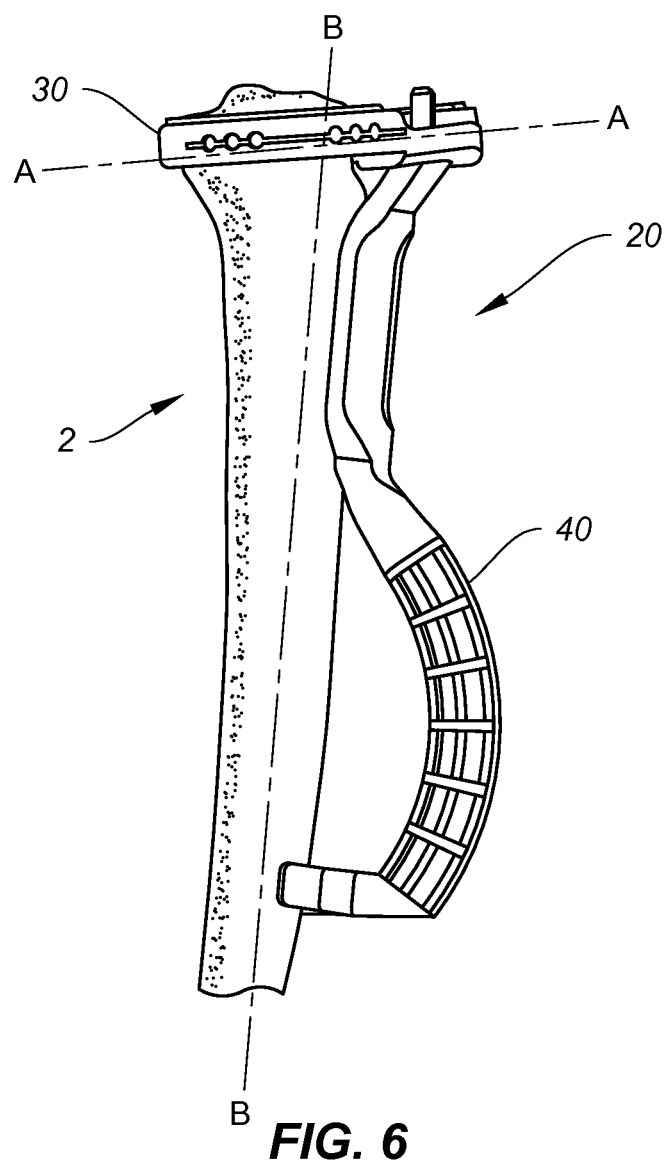
FIG. 6 shows a side view of the navigation instrument of FIG. 1 relative to a tibia.

FIG. 6 shows a side view of the fit of the guide 30 onto the tibia 2. The anterior-posterior slope angle of the tibial plateau is fixed and built into the guide handle connection 40, as represented by the broken lines representing the plateau axis A-A and the tibial axis B-B in FIGS. 6 and 10.

Figure 7B:
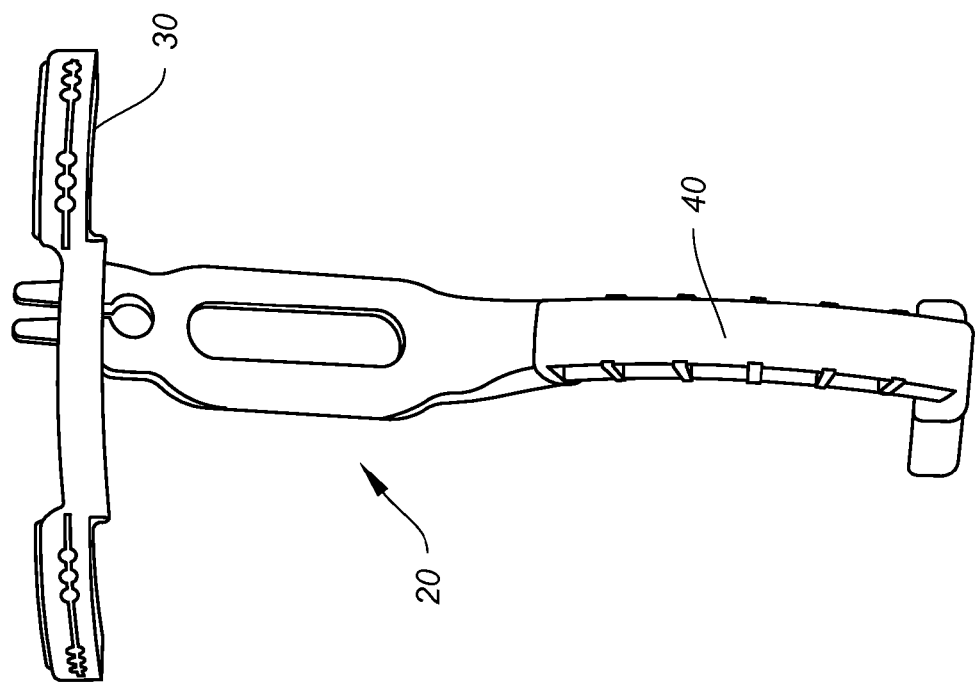
FIGS. 7A and 7B show a side perspective view of the navigation instrument of FIG. 4 and a front perspective view of the navigation instrument of FIG. 4, respectively.
Figure 7A:
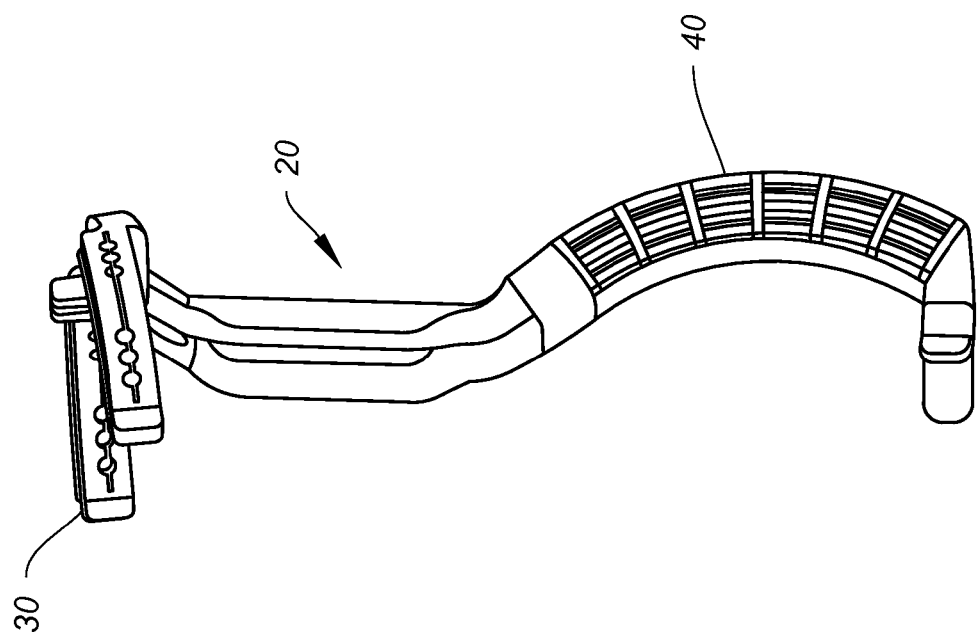
Figure 8:
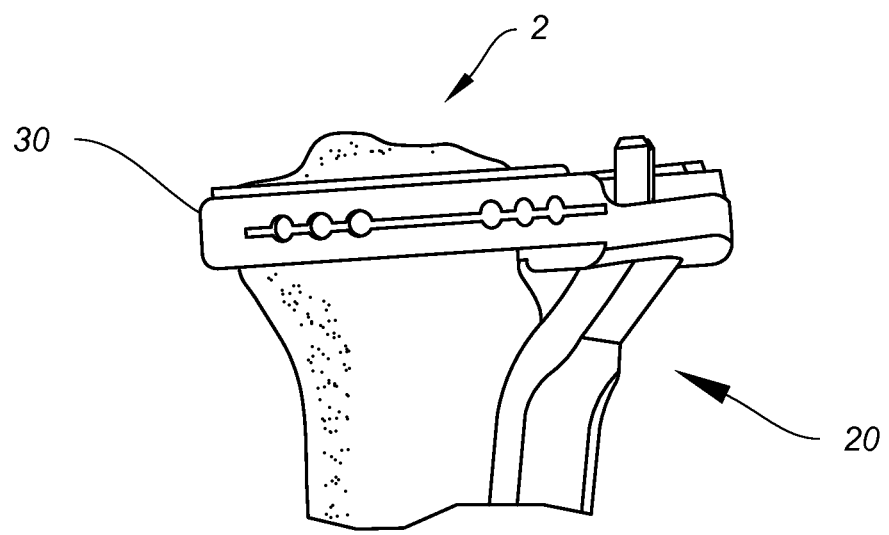
FIG. 8 shows a partial cutaway view of the navigation instrument of FIG. 4 relative to a tibia.
Figure 9:
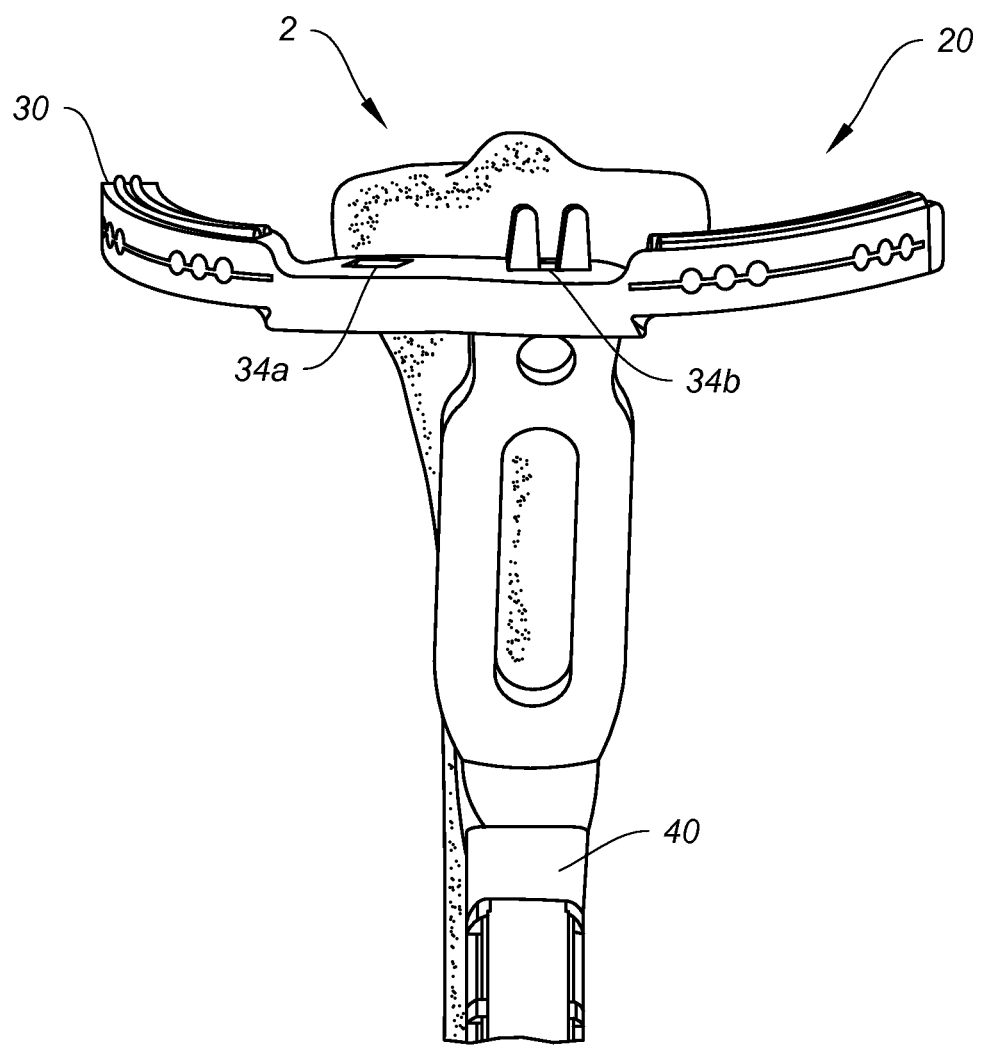
FIG. 9 shows a front perspective view of the navigation instrument of FIG. 4 relative to a tibia.
Figure 10:
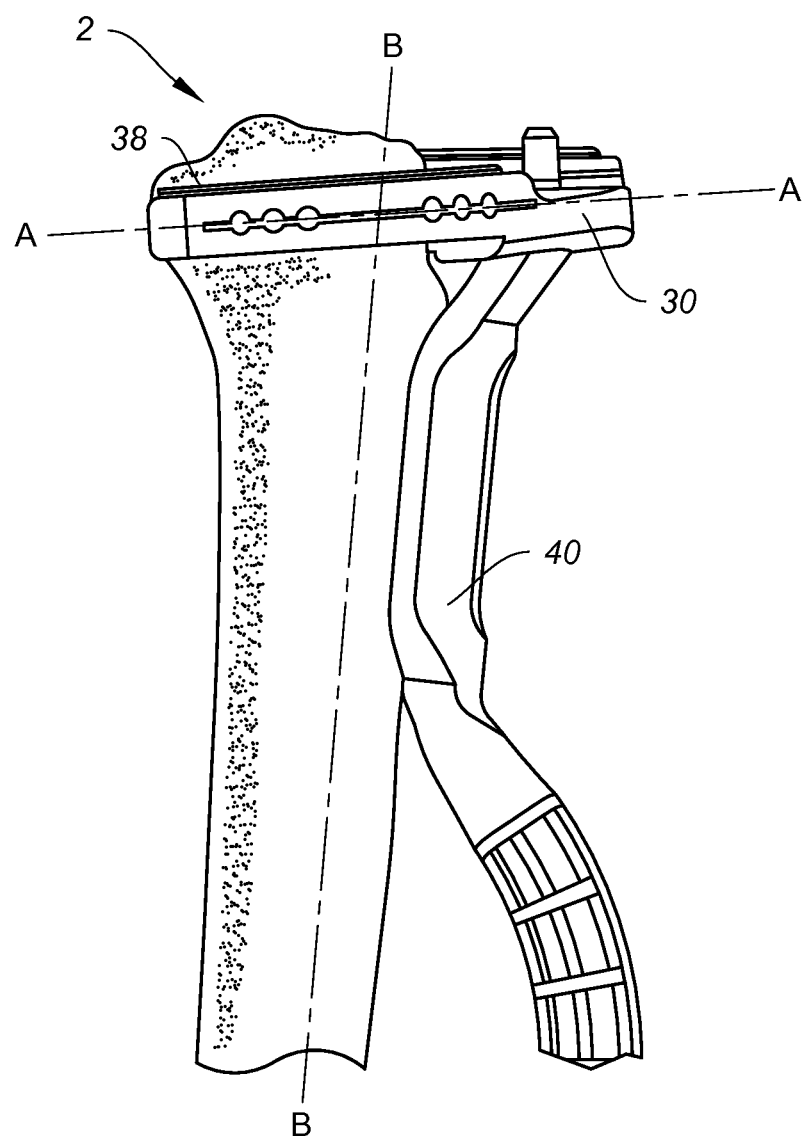
FIG. 10 shows a side perspective view of the navigation instrument of FIG. 4 relative to a tibia.
Figure 11:
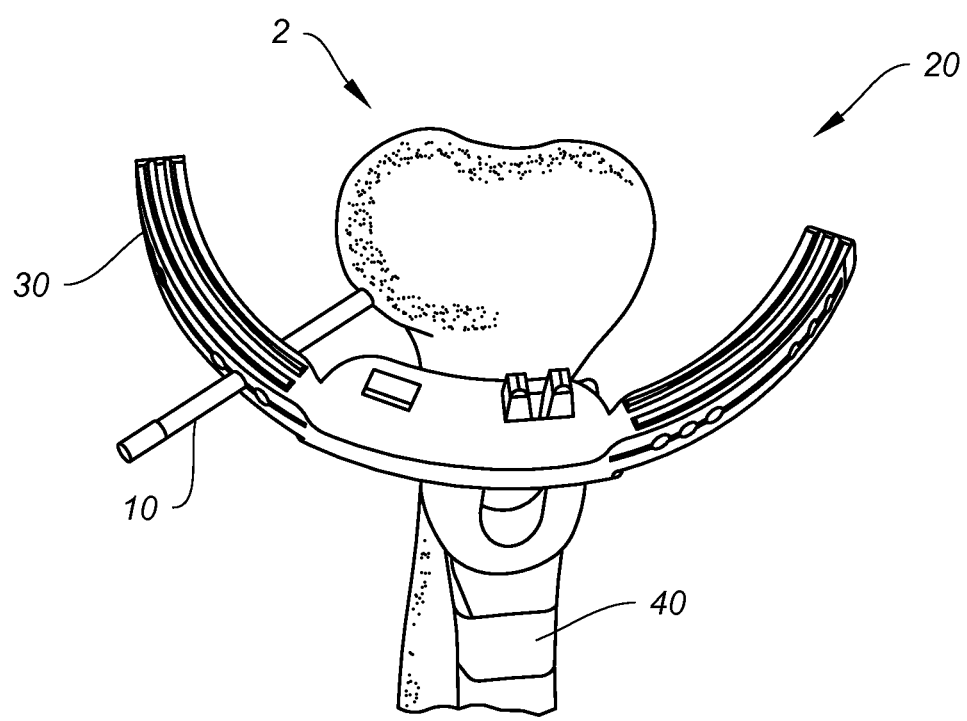
FIG. 11 shows a perspective view of the navigation instrument of FIG. 4 with delivery pin relative to a tibia.

FIGS. 7A and 7B show side and front views of the guide 30 and handle 40 of the instrument 20 without the tibia bone, respectively, while FIG. 8 shows the side view of the instrument and guide 30 positioned relative to the tibial bone 2. The guide component 38 may have internal radio-opaque lines/markers 38 to help vertically align the guide 30 with the top of the tibial plateau, as shown in FIG. 10. Further, as shown in FIG. 9, the guide 30 and handle 40 are attachable and detachable for Left and Right Knee orientation via right slot 34a and left slot 34b on the guide 30. Once the guide 30 is held in place with alignment to the tibial plateau, a depth control sleeve and injection needle 10 can be inserted through the guide 30 into the targeted area of the bone 2, as shown in FIG. 11.

Figure 12B:
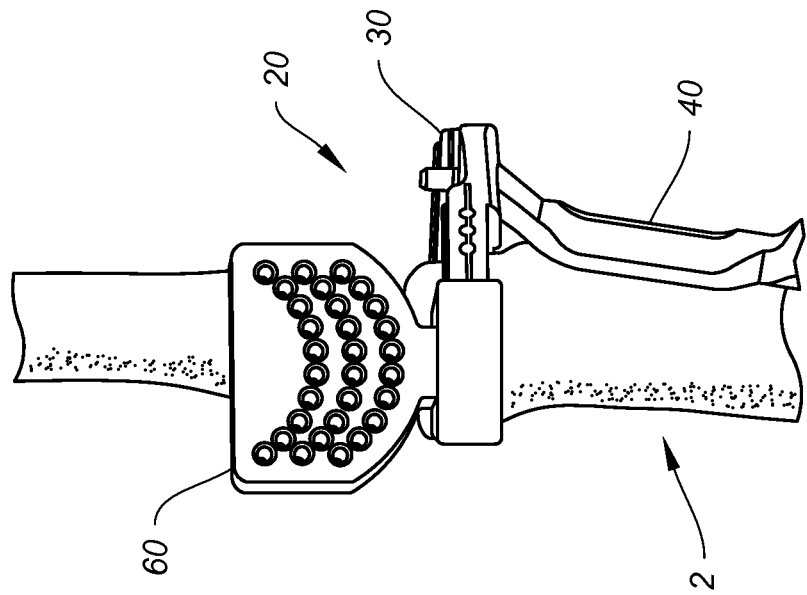
FIG. 12B shows another perspective view of the navigation instrument of FIG. 12A relative to a femur.
Figure 12A:
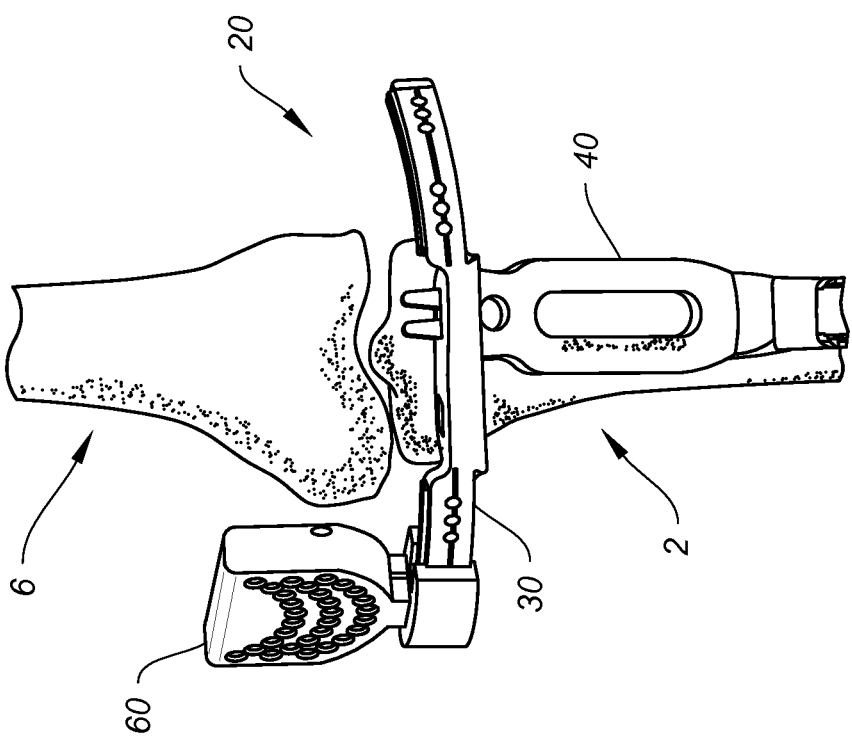
FIG. 12A shows a perspective view of another exemplary embodiment of a navigation instrument of the present disclosure relative to a femur.

FIGS. 12A and 12B show an exemplary embodiment of the navigation instrument 20 configured for use with a femur 6. For treatment of the femur 6, a femoral guide 60 can be attached to the side of the guide 30 for direct lateral approach to the distal femur 6, as shown. The side profile would appear over the distal femur in x-ray and radio-opaque markers would aide the user in selecting the appropriate trajectory and corresponding portal into the femur 6.

The tibial navigation instrument 20 includes a guide 30 that contours to an average tibial tuberosity 4. Further, the guide 30 already includes M/L tibia tilt; A/P tibia tilt; and axial rotation. There is no need for posterior edge alignment due to depth gauge used with injection needle 10. In an exemplary method of using the instrument, the surgeon would mark the joint line from a sagittal view, and rest the guide on the tibia, defaulting to the contoured shape. The surgeon would match the height of the joint line and, under C-arm visualization, make final adjustments. Then, the injection pin and depth gauge (with optional C-arm visualization to confirm depth) are drilled into the bone.

An exemplary method of using the femoral navigation instrument 20 with attached femoral guide 60 is similar to the tibial technique described above. The femoral guide 60 is initially put in its more comfortable position. The femoral guide position is then aligned with the femoral condyle in a lateral view. The delivery pin or needle with depth gauge 10 is then drilled into the target location through the portal of the guide 60 (with optional C-arm visualization to confirm depth).

It is contemplated that the delivery pin of the present disclosure may be similar to those disclosed in co-pending and co-owned U.S. Patent Application Publication No. 2012/0316513, filed Jun. 8, 2012 and entitled "INSTRUMENTS AND DEVICES FOR SUBCHONDRAL JOINT REPAIR," and further include adapter and components as described in this application. Likewise, as mentioned above, the pin may incorporate various depth control features or components. Additional depth control features or components that may be incorporated into the systems and methods of the present disclosure are disclosed in U.S. patent application Ser. No. 14/021,785 filed on Sep. 9, 2013 and entitled "INSTRUMENTS FOR CONTROLLED DELIVERY OF INJECTABLE MATERIALS INTO BONE." The contents of both these applications are herein incorporated in their entirety by reference.

Figure 13A:
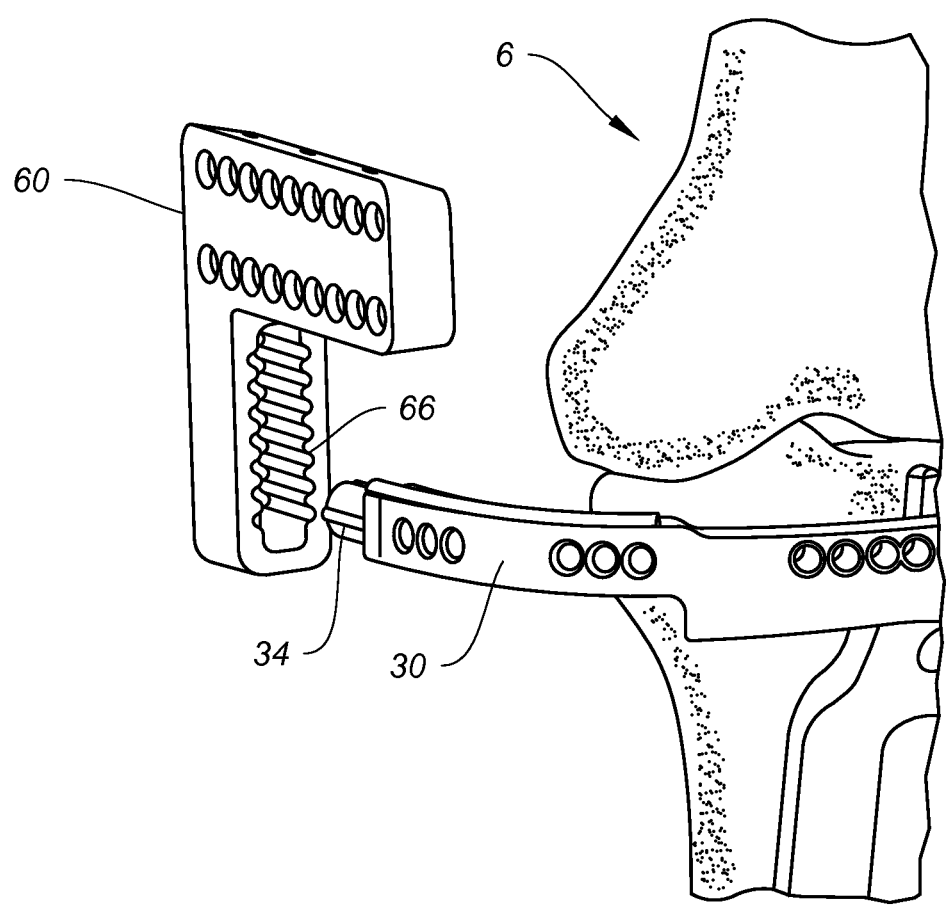
FIGS. 13A-13C show various perspective views of still another exemplary embodiment of a navigation instrument for use with a femur.
Figure 13C:
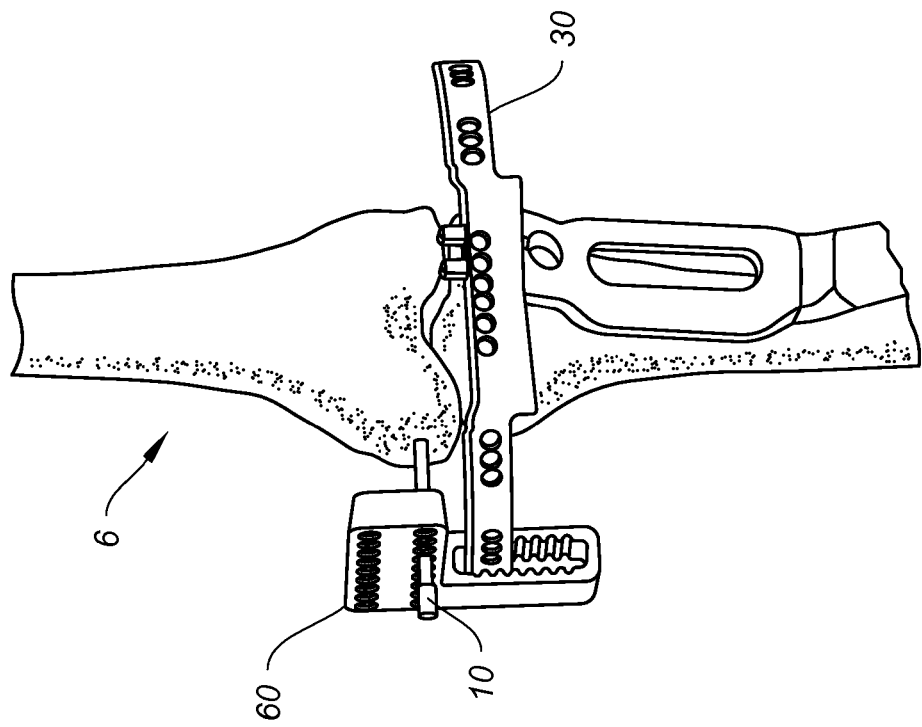
Figure 13B:
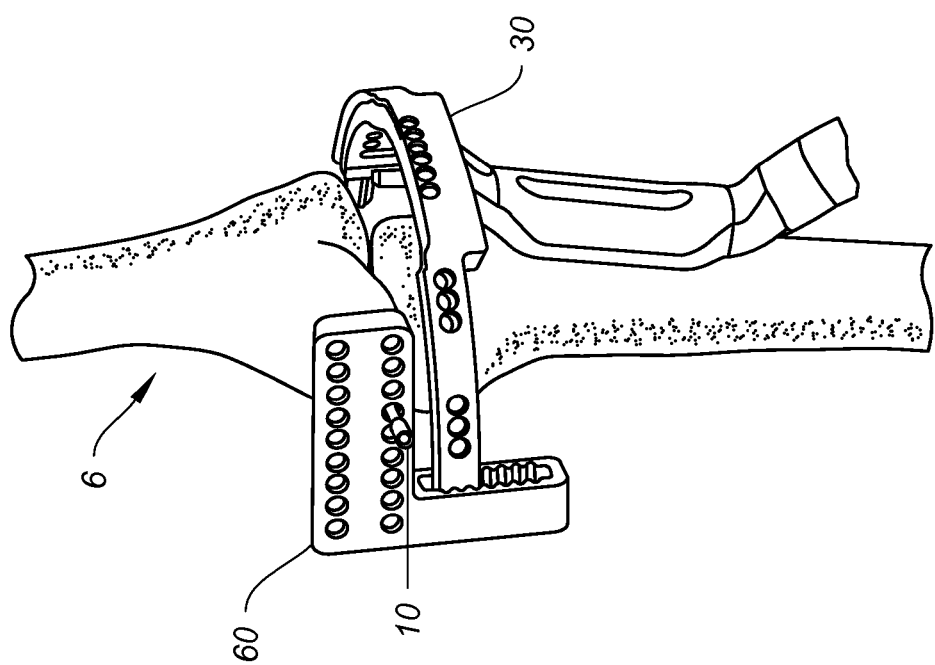

FIGS. 13A-13C show still another embodiment of a femoral navigation instrument 20 allowing easy adjustment and attachment of the femoral guide component 60 to the guide 30. As shown in FIG. 13A, the guide 30 may have a notch 34 for mating with a slot 66 on the femoral guide component 60. Both the notch 34 and slot 66 may be shaped and keyed to fit one another. The user may adjust the height of the femoral guide component 60 relative to the guide 30 easily by sliding the component 60 on and off the notch 34. Once the proper height is achieved, the depth control sleeve and needle 10 may be drilled through the femoral guide component 60, as shown in FIGS. 13B and 13C.

The previous embodiments of navigation instruments, both tibial and femoral versions, are directed to frame navigation. The next embodiments of navigation instruments are directed to free hand navigation. In this instance, instead of a guide with multiple holes to target the different zones or locations in the bone, the guide has a single portal configuration with multiple reference marks that correlate to an anatomical reference point. A template is used to map the tibia and determine which trajectory to use. By aligning the chosen guide mark with the anatomical reference, the portal trajectory is aligned to the intended target zone.

Figure 14A:
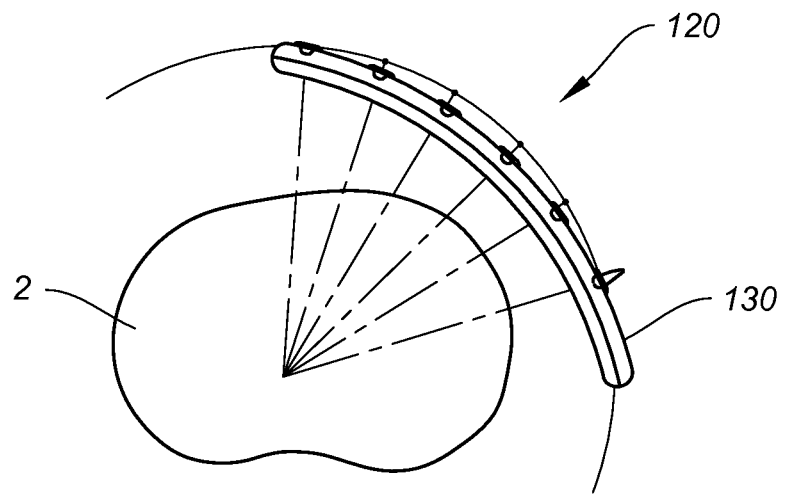
FIG. 14A shows a top-down view of still another exemplary embodiment of a navigation instrument of the present disclosure relative to a femur.
Figure 14B:
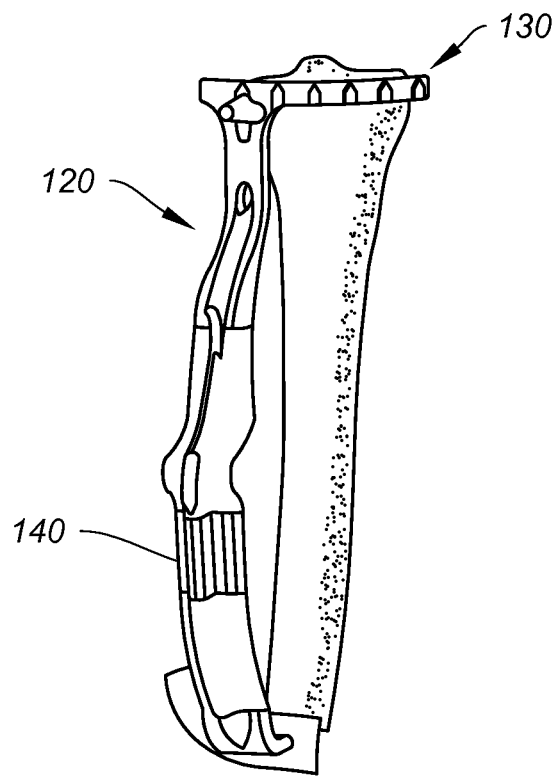
FIG. 14B shows a perspective view of the navigation instrument of FIG. 14A relative to a tibia.
Figure 14C:
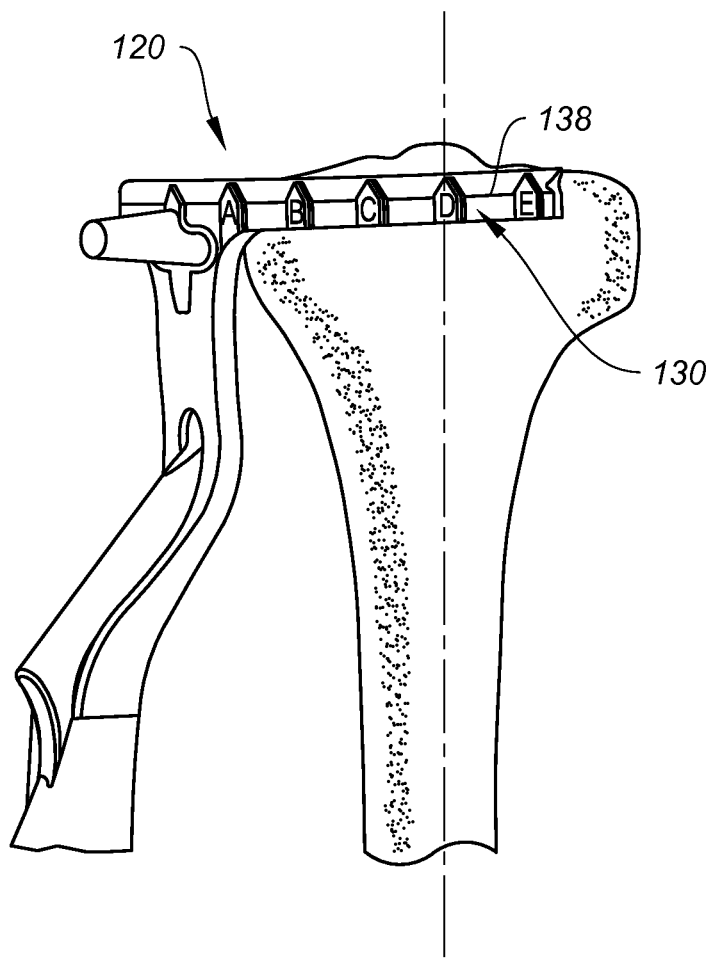
FIG. 14C shows an enlarged view of the navigation instrument of FIG. 14B relative to a tibia.
Figure 14E:
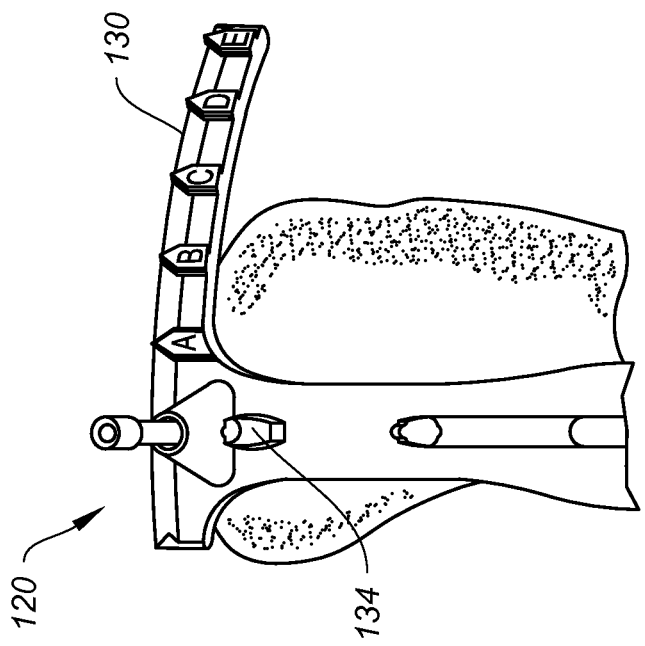
FIG. 14E shows another perspective view of the navigation instrument and needle of FIG. 14D relative to a tibia.
Figure 14D:
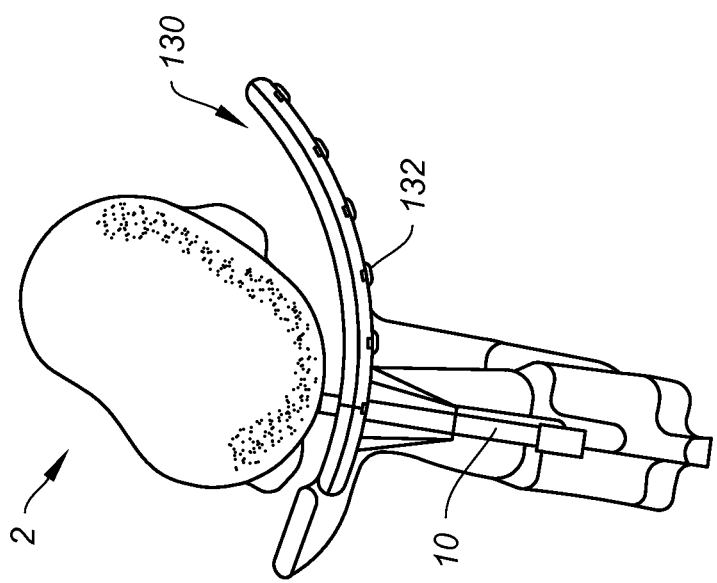
FIG. 14D shows a top-down perspective view of the navigation instrument of FIG. 14B in use with a needle relative to a tibia.
Figure 14F:
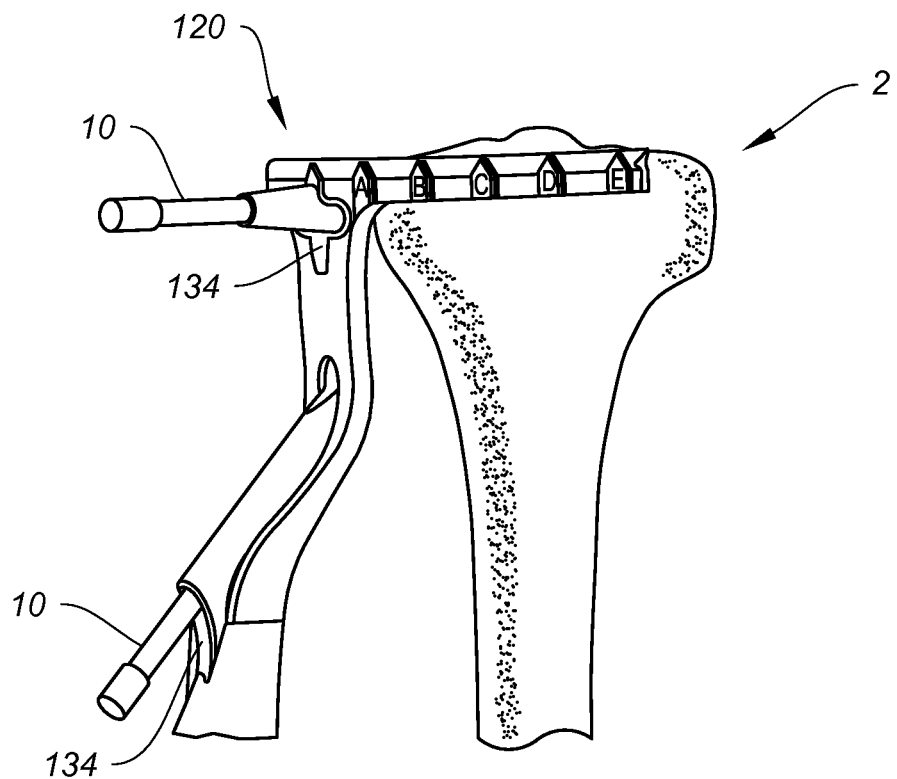
FIG. 14F shows a perspective view of the navigation instrument of FIG. 14B in use with an injection needle relative to a tibia.
Figure 14G:
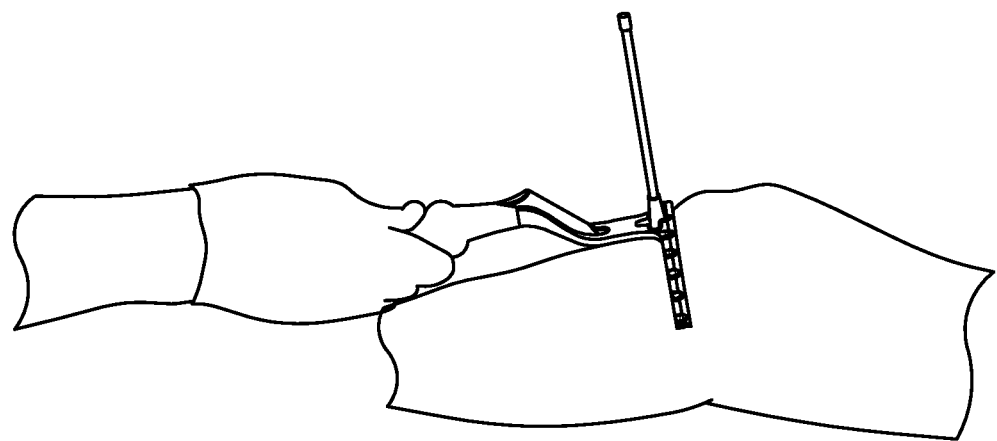
FIG. 14G shows the navigation instrument with needle of FIG. 14B relative to the patient's leg.

The template alignment zones or guide 130 would appear something similar to what is shown in FIG. 14A. FIG. 14B shows a full-length view of the navigation instrument 120 with a single component handle 140 and guide 130 with markings 132. The handle 140 is made to fit securely at each end onto the leg surface to align with the tibia 2. The guide 130 may include horizontal radiopaque markers 138 that can be aligned with the center notch of the tibial plateau in the x-ray A/P view, as shown in FIG. 14C. Once the instrument 120 is aligned, a depth sleeve and injection needle 10 can be inserted into bone through the guide 130, as shown in FIGS. 14D and 14E. As FIG. 14F illustrates, this guide 130 may also include one or more slots 134 configured with a size and shape that allows for insertion of a scalpel; this eliminates the need to move the guide 130 to cut the skin with the scalpel and decreases chances of error. Two different choices of needle trajectory are provided in the guide 130 for a direct horizontal and angled distal approach, as shown in FIG. 14F. FIG. 14G shows the instrument positioned against a patient's leg and a needle inserted through one of the slots.

It is contemplated that the surgeon would use a template to choose a trajectory to the subchondral bone defect, such as a bone marrow lesion or edema, and under fluoroscopic visualization align the instrument 120 to the plateau. Next, the skin is cut with a scalpel through the port, and a delivery pin with desired depth gauge may be power drilled into the targeted location (with optional perpendicular view to confirm).

Figure 15A:
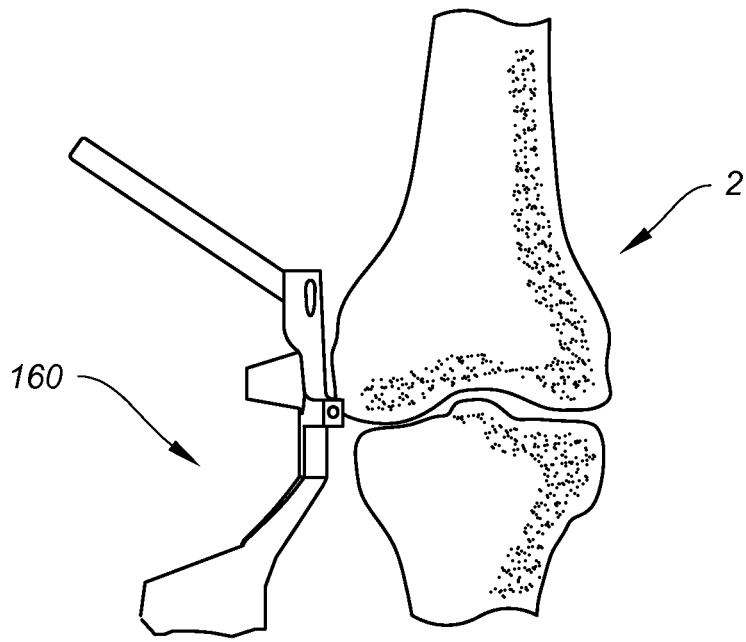
FIGS. 15A-15C show perspective views of another embodiment of a navigation instrument of the present disclosure relative to a femur.
Figure 15B:
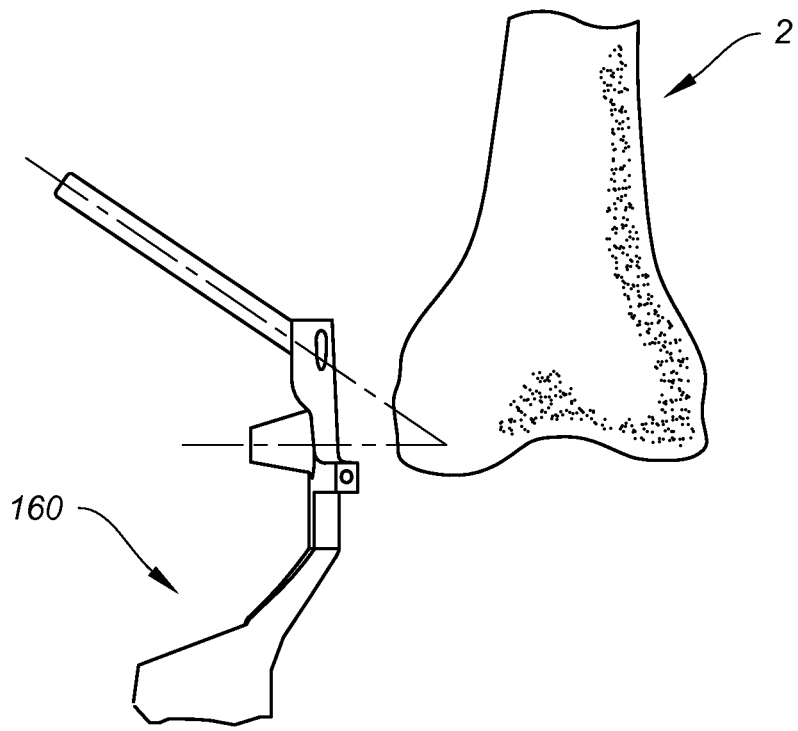
Figure 15C:
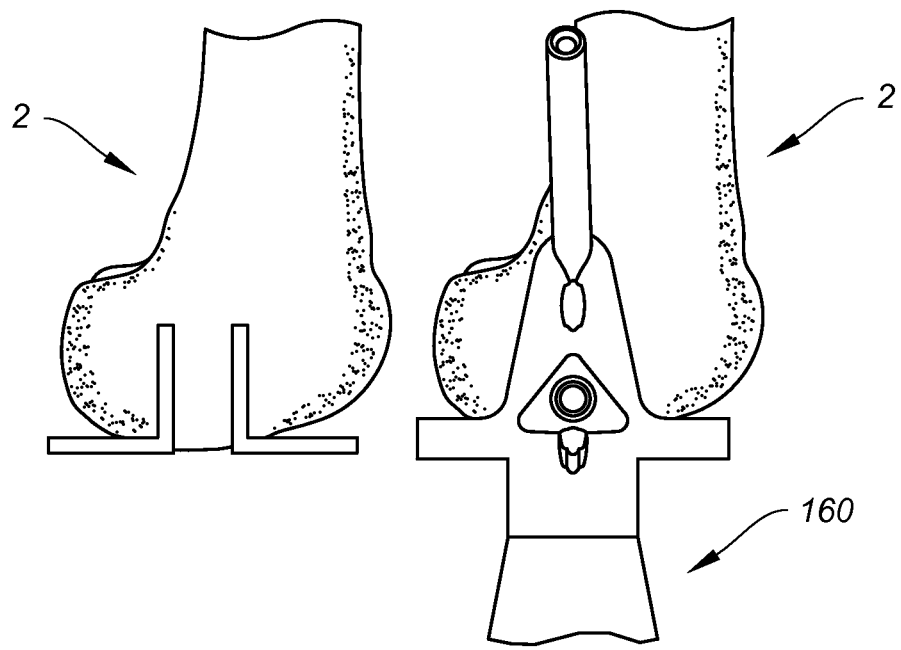

FIGS. 15A-15C show a femoral version of the navigation instrument 120. Treatment of the femur 6 may employ a simple guide 160 with similar single injection trajectory, as shown in FIGS. 15A and 15C; radiopaque markers may be provided with the guide 160 to help position the guide 160 in the x-ray lateral view against the side of the femur 6, as shown in FIG. 15B. In the femoral procedure, using a sagittal view, the surgeon may mark the surface tangent to the femur 6 where injection is desired. Then the surgeon would align the fluoroscopic markers to match, use a scalpel to cut the skin through the port, and power drill a delivery pin with desired depth gauge into the targeted location (with optional perpendicular view to confirm).

Figure 16:
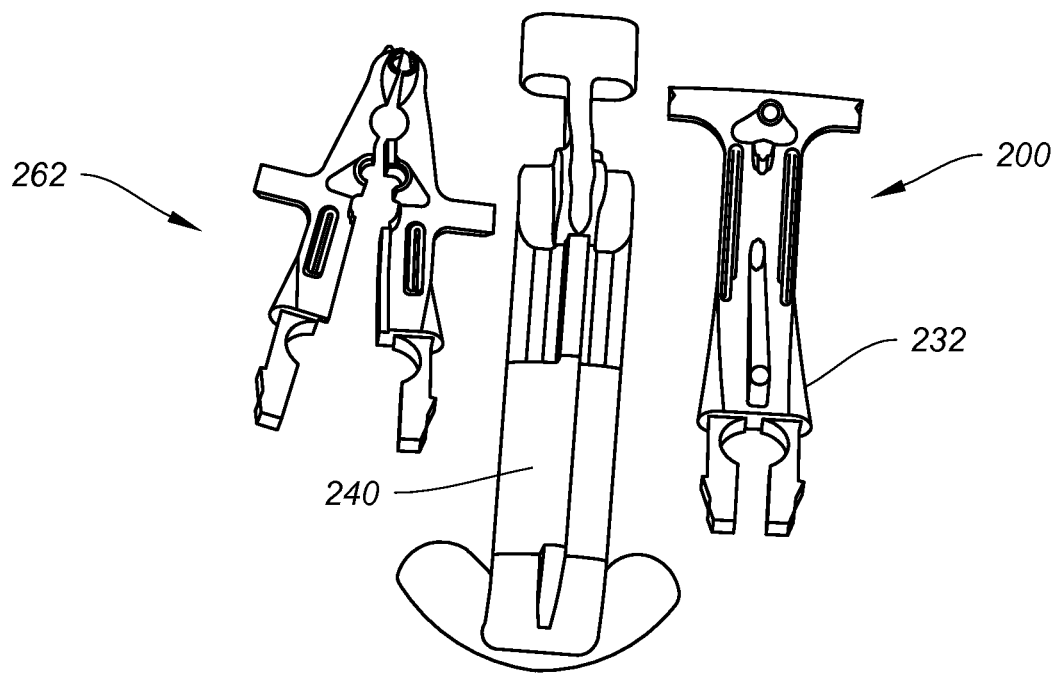
FIG. 16 shows an exemplary embodiment of a guide system comprising various components for assembling a femoral or tibial guide instrument of the present disclosure.

FIG. 16 shows a system 200 comprising various components for assembling a tibial guide instrument 220 (FIG. 17) or femoral guide instrument 260 (FIGS. 18A and 18B) of the present disclosure. The system 200 may include a handle 240 that receives either one of a tibial guide component 232 or a femoral guide component 262. One will recognize that the guide components 232, 262 include many of the features already described above for the guide instruments 120, 160, such as slots for receiving a scalpel that can also receive the depth gauge sleeve and needle 10. The guides are interchangeable and easily attachable to the handle 240, making the system highly adaptable to different uses.

Figure 17:
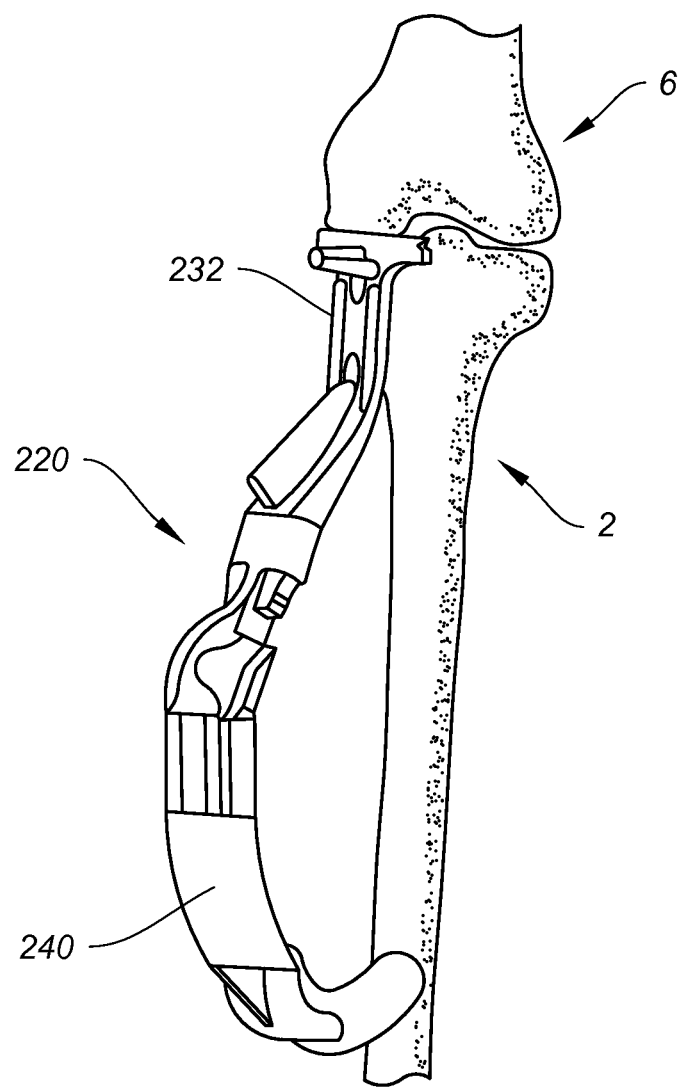
FIG. 17 shows a perspective view of an exemplary tibial guide instrument assembled from the system of FIG. 16 in use.

FIG. 17 shows a tibial guide instrument 220 assembled from the system 200 of FIG. 16. The tibial guide instrument 220 includes the tibial guide 232 inserted into the handle 240. The instrument 220 is shown braced against the leg of the patient.

Figure 18A:
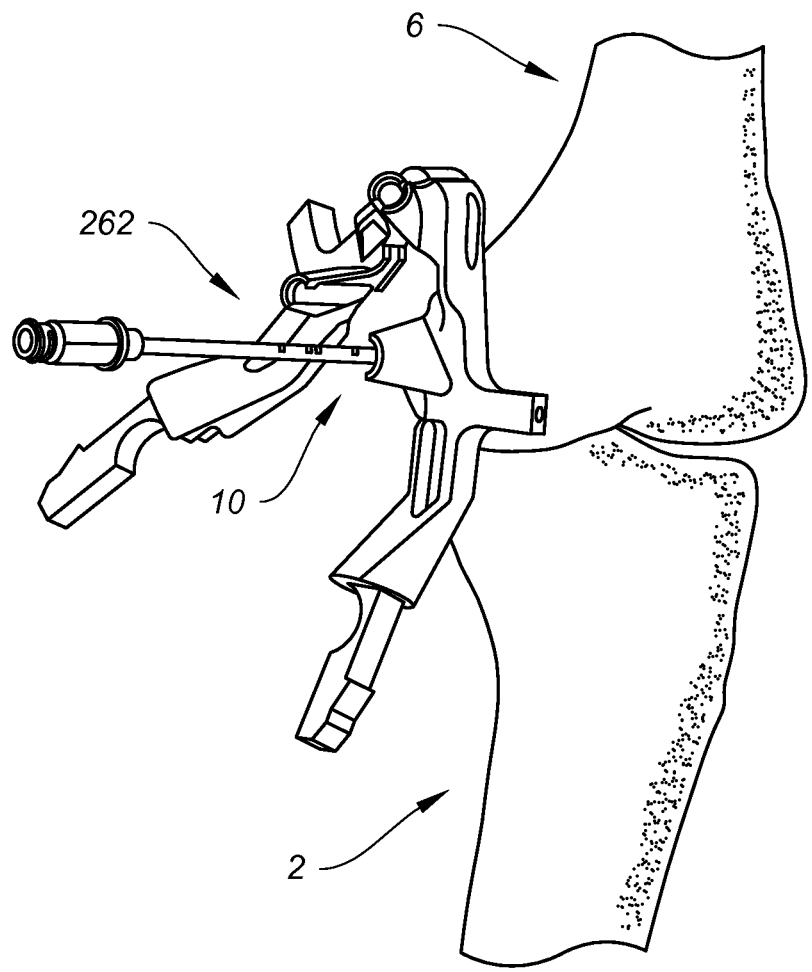
FIGS. 18A and 18B show a method of using an exemplary femoral guide instrument assembled from the system of FIG. 16.
Figure 18B:
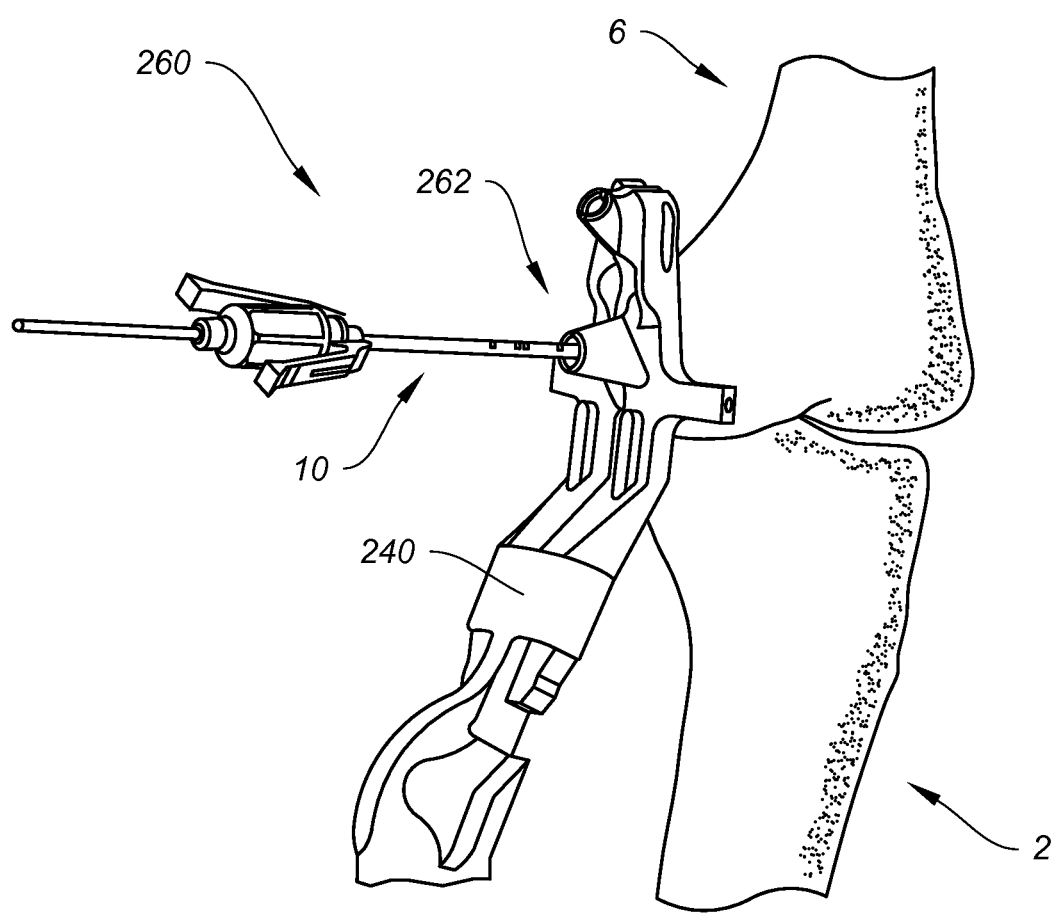

FIGS. 18A and 18B show a femoral guide instrument 260 assembled from the system 200 of FIG. 16. As shown in FIG. 18A, the femoral guide 262 may comprise hinged arms and allow a pin or needle 10 to be placed into the femur 6 in the open position of the femoral guide 262. FIG. 18B shows the femoral guide instrument 260 in which the femoral guide 262 is inserted into the handle 240, with the instrument 260 braced against the patient's leg.

Figure 19A:
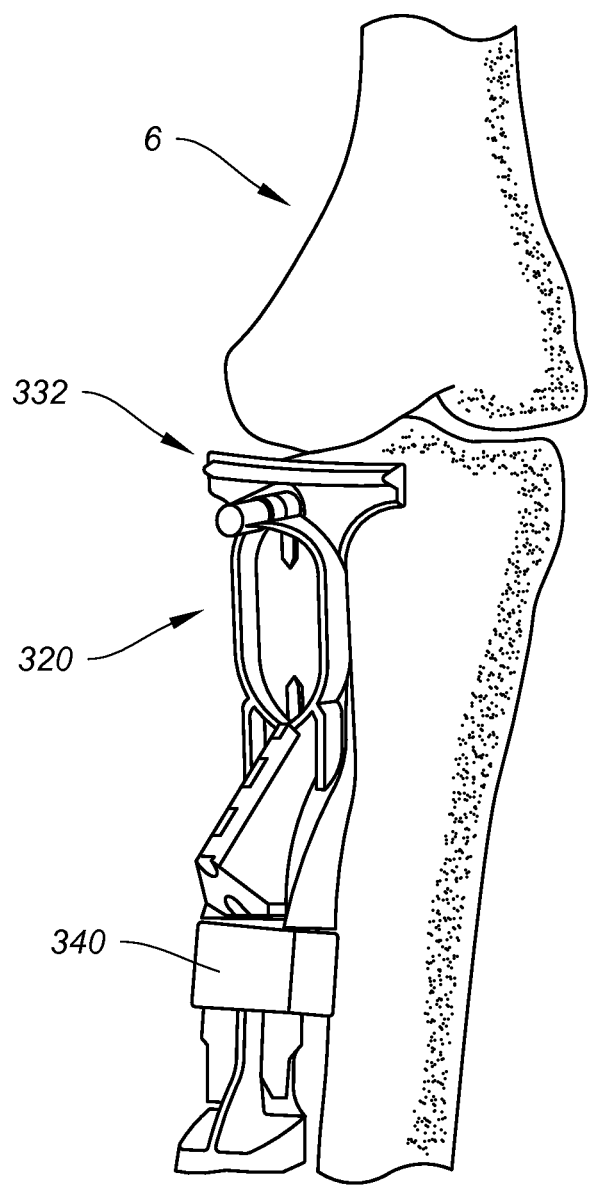
FIG. 19A shows a perspective view of another exemplary embodiment of a navigation instrument relative to a tibia.
Figure 19B:
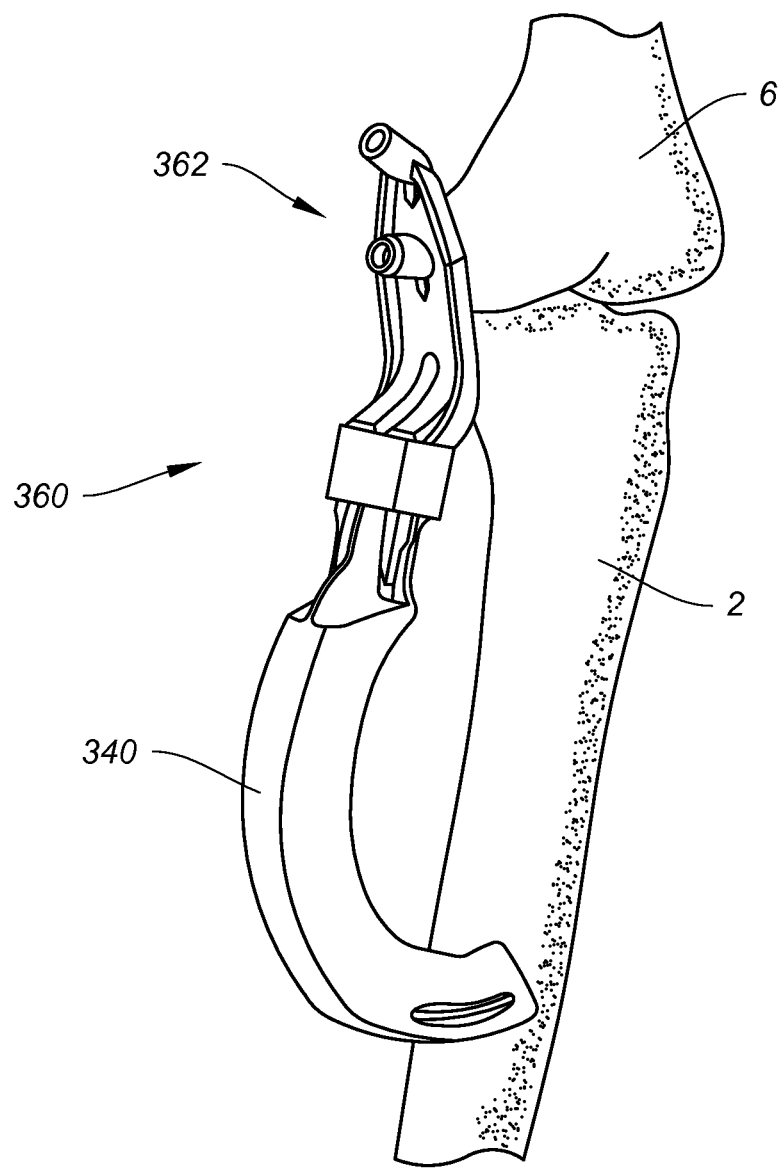
FIG. 19B shows a perspective view of another exemplary embodiment of a navigation instrument relative to a femur.

FIGS. 19A and 19B show other exemplary embodiments of guide instruments of the present disclosure. FIG. 19A shows a tibial guide instrument 320 assembled by inserting a tibial guide 332 into handle 340 similar to the manner described above. The tibial guide instrument 320 may be braced against the patient's knee in a manner similar to the one shown in FIG. 17. FIG. 19B shows a femoral guide instrument 360 assembled by inserting a femoral guide component 362 into handle 340 similar to the manner described above.

Figures 20, 21A:
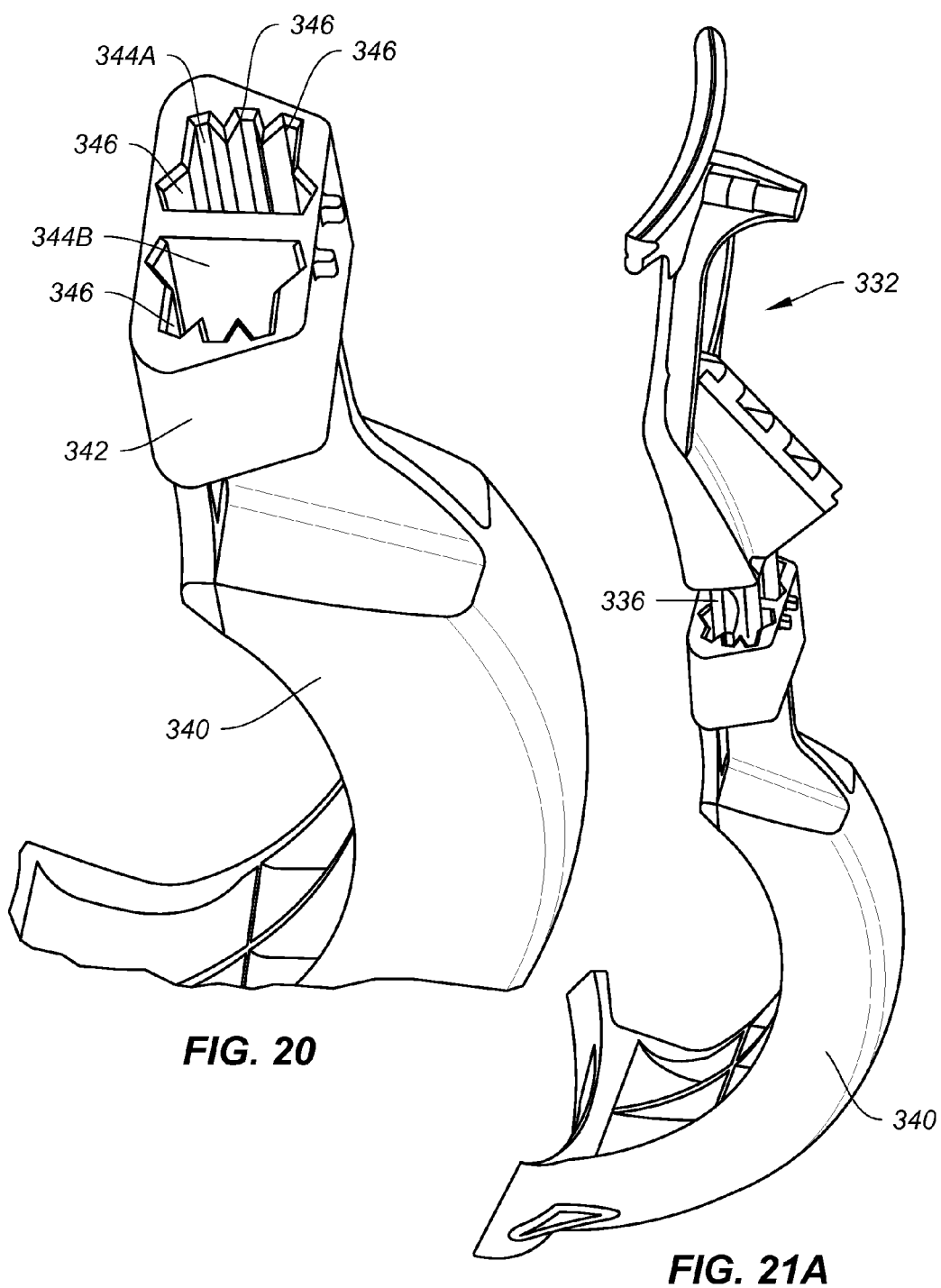
FIG. 20 shows an enlarged view of the handle of the navigation instrument of FIGS. 19A and 19B.
FIGS. 21A-21C show an exemplary method of assembling the navigation instrument of FIG. 19A.
Figures 21B, 21C:
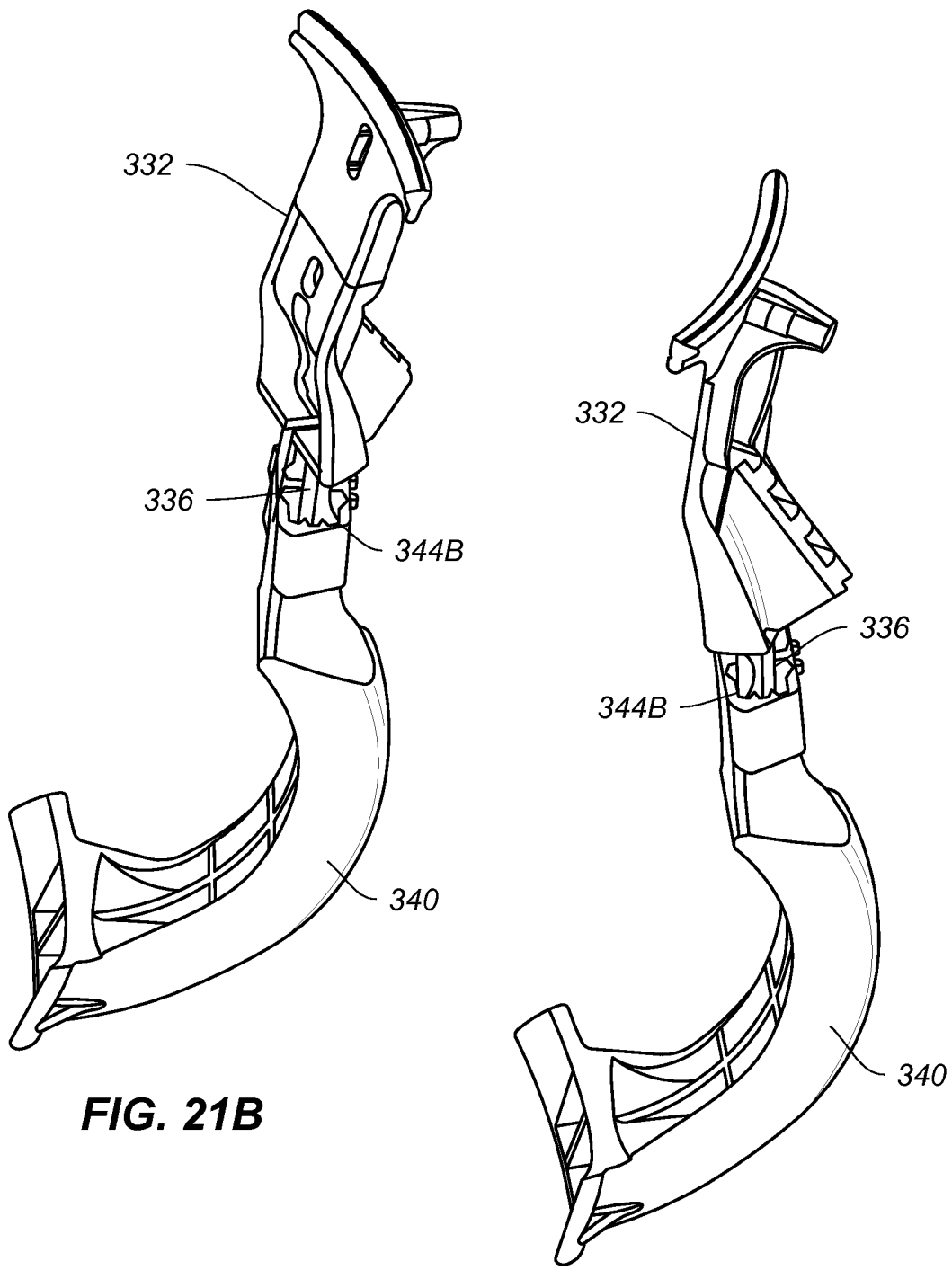

The guide instruments 320, 360 of FIGS. 19A and 19B have the ability to be angularly adjustable. As shown in FIG. 20, the handle 340 may comprise an attachment end 342 within which are slots or cutaway portions 344A, 344B. Each of the cutaway portions 344A, 344B also includes keyed sections or shaped notches 346. This allows a complementarily shaped or fluted stem 336 on the guide components 332, 362 to be inserted at an angle with respect to the handle 340 by engaging the stem 336 with selected notches 346. For instance, as shown in FIG. 21A, the tibial guide component 332 may be attached to the handle 340 straight. As shown in FIGS. 21B and 21C, the tibial guide component 332 can also be angled relative to the handle 340 by sliding the tibial guide component 332 at an angle into the slots 344A, 344B. The ability to angle the guide components 332, 362 relative to the handle 340 enables customization to the patient's anatomy, and better conformity to a left or right knee.

The present navigation instruments simplify the process of mapping to an edema while also keeping a pin subchondral with faster, simpler positioning requirements using easy anatomical reference points. For instance, the instruments can be oriented to the tibial tuberosity. The complexity is built into the guide with built in anatomical angles specific to the left or right tibia. That is, the frame navigation-focused instruments provide preset anatomical planes for the frame to be simple and save time. All that is needed is to determine the height relative to the tibial plateau.

Alternatively the amount of precision is reduced to simplify the placement of the guide. For both guides the result is a "point and shoot" method that reduces the time and complexity in the technique. The new embodiments are intended to be simple one or two-piece designs. For instance, the free hand-focused instruments combine a scalpel hole with a drill hole, and allows "clocking" of the drill hole relative to the edema or map target, can be located off the mid-line, and can work in multiple planes of imaging planes.

In some embodiments, the guide may be marked in terms of absolute numerical values to additionally serve as a ruler-like function. This would allow the guide to still be used on many different sized knees, where the distance to the center of the knee may be determined along with the distance to the edema (such as from MRI software that can calculate the distance of the edema from the knee's center). Then, using the guide as a ruler, the user is able to determine the location of the edema according to the distance markers of the guide.

In still other embodiments, the markings on the guide may be proportionally distanced relative to the knee size to allow for size fluctuations. Thus, accounting for this size differential in the markings along the guide would prove beneficial.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A system for navigating to a target area near a subchondral defect of a bone, comprising:
   one or more guide components having an engaging end, the one or more guide components including one or more device portals, each device portal defining a trajectory and configured to provide accurate and controlled delivery of a tool to the target area;
   a detachable handle including an attachment end having a slot to slidingly receive the engaging end of the one or more guide components, wherein the one or more guide components are a tibial guide component and includes a notch at an end of the guide, and when the tibial guide component is coupled to the handle, an angle of the guide relative to the handle includes an anterior-posterior slope angle of a tibial plateau of a patient; and
   a femoral guide configured to attached to the tibial guide component, the femoral guide including at least one device portal and a plurality of slots, each one of the plurality of slots configured to receive the notch of the tibial guide component.

2. The system of claim 1, wherein the one or more guide components are angularly adjustable with respect to the handle.

3. The system of claim 1, wherein the slot of the handle includes a plurality of keyed notches.

4. The system of claim 3, wherein the engaging end of the one or more guide components is shaped to engage one or more of the keyed notches of the slot of the handle.

5. The system of claim 1, wherein the one or more guides includes a femoral guide component.

6. The system of claim 1, wherein the tool is an injection needle.

7. The system of claim 6, further including:
a depth gauge for use with the injection needle.

8. The system of claim 1, wherein the one or more guides include visual markers to assist in positioning the instrument.

9. An instrument for navigating to a target area near a subchondral defect of a bone, comprising:
a guide having a plurality of device portals, each portal defining a trajectory and configured to provide accurate and controlled delivery of a tool to the target area, wherein the guide is a tibial guide and includes a notch at an end of the guide;
a handle extending from the guide; and
a femoral guide configured to attach to the tibial guide, the femoral guide including at least one device portal and a plurality of slots, each one of the plurality of slots configured to receive the notch of the tibial guide;
wherein the instrument is configured to be aligned with an anatomical landmark of the bone, and
wherein an angle of the guide relative to a tibial axis includes an anterior-posterior slope angle of a tibial plateau.

10. The instrument of claim 9, wherein the handle is detachable from the guide.

11. The instrument of claim 9, wherein the guide includes visual markers for vertical alignment of the guide relative to the handle.

12. The instrument of claim 9, wherein the guide includes a first slot and a second slot, the handle configured to attach to the guide at one of the first slot and the second slot.

13. A system for navigating to a target area near a subchondral defect of a bone, comprising:
a handle having a guide attachment end, the handle configured to align with a tibial axis and a tibial tuberosity of a tibia;
a tibial guide component including a plurality of device portals, a first slot, and a second slot, each first device portal defining a trajectory and configured to provide accurate and controlled delivery of a tool to a target area near a subchondral defect of the tibia, wherein the first slot and the second slot are configured to receive the engaging end of the handle to releasable couple the handle to the tibial guide component, wherein, when the tibial guide component is coupled to the handle, an angle of the tibial guide component relative to the handle includes an anterior-posterior slope angle of a tibial plateau of a patient; and
a femoral guide component configured to be releasably coupled to the tibial guide component, the femoral guide component including a plurality of device portals, each portal defining a trajectory and configured to provide accurate and controlled delivery of the tool to a target area near a subchondral defect of the femur, wherein the femoral guide component includes a plurality of slots that are configured to receive a keyed notch of the tibial guide component to adjust the height of the plurality of device portals of the femoral guide component with respect to the tibial guide component.

14. The system of claim 13, wherein the tibial guide component includes a bone contouring surface that contours to the anatomical landmark of the tibia.

15. The system of claim 13, wherein first slot of the tibial guide component is a right knee configuration and the second slot of the tibial guide component is a left knee configuration.

* * * * *